(12) United States Patent
Bartee et al.

(10) Patent No.: US 7,933,849 B2
(45) Date of Patent: Apr. 26, 2011

(54) INTEGRATED MODEL PREDICTIVE CONTROL OF BATCH AND CONTINUOUS PROCESSES IN A BIOFUEL PRODUCTION PROCESS

(75) Inventors: James F. Bartee, Stilesville, IN (US); Maina A. Macharia, Round Rock, TX (US); Patrick D. Noll, Richardson, TX (US); Michael E. Tay, Georgetown, TX (US)

(73) Assignee: Rockwell Automation Technologies, Inc., Mayfield Heights, OH (US)

( * ) Notice: Subject to any disclaimer, the term of this patent is extended or adjusted under 35 U.S.C. 154(b) by 777 days.

(21) Appl. No.: 11/928,186

(22) Filed: Oct. 30, 2007

(65) Prior Publication Data

US 2008/0109200 A1     May 8, 2008

Related U.S. Application Data

(60) Provisional application No. 60/863,759, filed on Oct. 31, 2006, provisional application No. 60/917,916, filed on May 14, 2007.

(51) Int. Cl.
*G06E 1/00*     (2006.01)
*G06E 3/00*     (2006.01)
*G06F 15/18*    (2006.01)
*G06G 7/00*     (2006.01)

(52) U.S. Cl. ........................................................ 706/19

(58) Field of Classification Search .................. 435/160; 706/19
See application file for complete search history.

(56) References Cited

U.S. PATENT DOCUMENTS 3,379,421 A     4/1968 Putman
(Continued)

FOREIGN PATENT DOCUMENTS

EP          0303345 A2     2/1989

OTHER PUBLICATIONS

Selvam P.V.P, 'Computer Aided Tools for Process Synthesus, Analysis and Optimium Design of Biofuel.' $4^{th}$ meeting of energy in rural areas, Brazilian Society of Agricultural Engineering—SBEA, Oct. 2002 [retrieved on Aug. 23, 2010]. Retrieved from the Internet<www.nipeunicamp.org.br/agrener/anais/2002/0067.pdf>.*

(Continued)

*Primary Examiner* — Donald Sparks
*Assistant Examiner* — Peter Coughlan
(74) *Attorney, Agent, or Firm* — Fletcher Yoder LLP; William R. Walbrun; John M. Miller

(57) ABSTRACT

System and method for managing a biofuel production process. An integrated dynamic multivariate predictive model is provided that includes a continuous process model representing a continuous process of the biofuel production process, a batch process model representing a batch process of the biofuel production process, and a continuous simulation framework. The batch process model interacts with the continuous process model as a nonlinear continuous process via the framework using bridging equations. An objective is received, as is constraint information specifying constraints for the biofuel production process, where the constraints are in terms of the framework, and process information related to the batch and continuous processes. The integrated model is executed per the objective using the process information as input, generating target values for variables related to the batch and continuous processes per the objective and subject to the constraints, and used to control the batch and continuous processes substantially optimally.

23 Claims, 12 Drawing Sheets

U.S. PATENT DOCUMENTS

| | | | |
|---|---|---|---|
| 4,309,254 | A | 1/1982 | Dahlstrom et al. |
| 4,358,346 | A | 11/1982 | Shinskey |
| 4,626,321 | A | 12/1986 | Grethlein et al. |
| 5,036,005 | A | 7/1991 | Tedder |
| 5,177,008 | A | 1/1993 | Kampen |
| 5,407,817 | A | 4/1995 | Lightsey et al. |
| 5,477,444 | A | 12/1995 | Bhat et al. |
| 5,932,456 | A | 8/1999 | Van Draanen et al. |
| 6,496,781 | B1 | 12/2002 | Chen et al. |
| 6,510,368 | B1 | 1/2003 | Beardwood et al. |
| 6,609,119 | B1 | 8/2003 | Meghlaoui |
| 6,792,336 | B1 | 9/2004 | Johnson et al. |
| 6,934,931 | B2 | 8/2005 | Plumer et al. |
| 2002/0077711 | A1 | 6/2002 | Nixon et al. |
| 2003/0040642 | A1 | 2/2003 | Goto et al. |
| 2004/0023349 | A1 | 2/2004 | Bisgaard-Frantzen et al. |
| 2004/0033457 | A1 | 2/2004 | Zhang et al. |
| 2005/0112739 | A1 | 5/2005 | Golubkov |
| 2005/0233030 | A1 | 10/2005 | Lewis et al. |
| 2005/0260553 | A1* | 11/2005 | Berzin ............ 435/3 |
| 2006/0225350 | A1 | 10/2006 | Spallone et al. |
| 2007/0078530 | A1 | 4/2007 | Blevins et al. |
| 2008/0028675 | A1 | 2/2008 | Clifford et al. |
| 2008/0103747 | A1 | 5/2008 | Macharia et al. |
| 2008/0103748 | A1 | 5/2008 | Axelrud et al. |
| 2008/0104003 | A1 | 5/2008 | Macharia et al. |
| 2008/0108048 | A1 | 5/2008 | Bartee et al. |
| 2008/0109100 | A1 | 5/2008 | Macharia et al. |
| 2008/0167852 | A1 | 7/2008 | Bartee et al. |

OTHER PUBLICATIONS

De Andres-Toro, B., et al., "Evolutionary Optimization of an Industrial Batch Fermentation Process", European Control Conference, 1997, http://www.cds.caltech.edu/conferences/related/ECC97/proceeds/501_750/ECC615.PDF, 6 pages.

De Andres-Toro, B, J.M Giron-Sierra, J.A. Lopez-Orozco, C. Ferandez-Conde, "Application of genetic algorithms and simulations for the optimization of batch fermentation control", Systems, Man, and Cybernetics, 1997. 'Computational Cybernetics and Simulation'., 1997 IEEE International Conference on Oct. 12-15, 1997, vol. 1, pp. 392-397.

Madar, Janos, Janos Abonyi, Balaz Balasko, Ferenc Szeifert, "Interactive Evolutionary Computation for Model Based Optimization of Batch Fermentation", European Control Conference, 1997, 6 pages.

State Technologies Advancement Collaborative, "Utilizing the National Corn-to-Ethanol Pilot Plant to Develop a Predictive Model for Distillers Dried Grain for the Fuel Ethanol and Animal Feed Industries", 2006, 6 pages, http://www.stacenergy.org/projects/04-STAC-01/04-2006-02.pdf, 6 pages.

Xiao, Jie, Ze-Kui Zhou, Guang-Xin Zhang, "Ant colony system algorithm for the optimization of beer fermentation control", Journal of Zhejiang University Science,ISSN 1009-3095, 2004, 5(12): pp. 1597-1603.

Chang, Raymond. "Physical Chemistry for the BioSciences; Chapter 10: Enzyme Kinetics", University Science Books, 2005, pp. 363-400.

Lin, Yan, Shuzo Tanaka, "Ethanol fermentation from biomass resources: current state and prospects", Appl. Microbiol. Biotechnol., 69: 627-642, 2006.

Lee, C.-G., C.H. Kim, S.K. Rhee, "A kinetic model and simulation of starch saccharification and simultaneous ethanol fermentation by amyloglucosidase and *Zymomonas mobilis*", Bioprocess Engineering 7, 1992, 335-341.

"Liquefaction of starch from dry-milled grains", Novozymes, 2004, 5 pages.

De Andres-Toro, B., J.M. Giron-Sierra, P. Fernandez-Blanco, J.A. Lopez-Orozco, E. Besada-Portas, "Multiobjective optimization and multivariable control of the beer fermentation process with the use of evolutionary algorithms", Journal of Zhejiang University SCIENCE, ISSN 1009-3095, 2004, 5(4): pp. 378-389.

De Andres-Toro, B., J.M. Giron-Sierra, J.A. Lopez-Orozco, C. Fernandez-Conde, J.M. Peinado, F. Garcia-Ochoa, "kinetic model for beer production under industrial operational conditions", Mathematics and Computers in Simulation 48, 1998, pp. 65-74.

U.S. Appl. No. 12/052,117, filed Mar. 20, 2008, Stephenson et al.
U.S. Appl. No. 12/052,159, filed Mar. 20, 2008, Stephenson et al.
U.S. Appl. No. 12/165,371, filed Jun. 30, 2008, Macharia et al.
U.S. Appl. No. 12/242,531, filed Sep. 30, 2008, Macharia et al.
U.S. Appl. No. 12/242,568, filed Sep. 30, 2008, Macharia et al.
U.S. Appl. No. 12/242,606, filed Sep. 30, 2008, Macharia et al.
U.S. Appl. No. 12/242,635, filed Sep. 30, 2008, Macharia et al.

De Filippis P. et al: "Transesterification Processes for Vegetable Oils: A Simple Control Method of Methyl Ester Content": Journal of the American Oil Chemists' Society, Springer, [Online] vol. 72, No. 11, Nov. 1999; pp. 1399-1404; URL:http://www.springerlink.com/content/content/104526532m44217/> [retrieved on Apr. 7, 2008] p. 1399-p. 1403.

Ghesti, G. F. et al: "Application of Raman Spectroscopy to Monitor and Quantify Ethyl Esters in Soybean Oil Transesterification"; Journal of the American Oil Chemists' Society, [Online] vol. 83, No. 7, Jul. 2006, pp. 597-601, XP002475273; Berlin / Heidelbert; ISSN: 0003-021X; Retrieved from the Internet: URL: http://www.springerlink.com/content/1h026742u8661135/> [retrieved on Apr. 7, 2008] p. 597-p. 600.

Grosman, et al: "Automated nonlinear model predictive control using genetic programming": Computers & Chemical Engineering, vol. 26, pp. 631-640 (2002).

Henson: "Nonlinear model predictive control: current status and future directions"; Computers & Chemical Engineering, vol. 23, pp. 187-202 (1998).

Kamm, et al.: "Principles of biorefineries;" Applied Microbiology and Biotechnology, vol. 64, pp. 137-145 (2004).

Miao, et al: "Nonlinear model predictive control based on support vector regression;" 2002 International Conference on Machine Learning and Cybernetics, vol. 3, pp. 1657-1661 (2003).

Onogi, et al: "An on-line operating control system for a class of combined batch/semi-continuous processes." Journal of Chemical Engineering of Japan, vol. 19, pp. 542-548 (1986).

Piche, et al.: "Nonlinear model predictive control using neural networks." Control Systems Magazine, IEEE, vol. 20, pp. 53-62 (2002).

Qin: "A survey of industrial model predictive control technology." Control Engineering Practice, vol. 11, pp. 733-764 (2003).

Raiko, et al.: "Learning nonlinear state-space models for control." IEEE Proceedings, 2005 IEEE International Joint Conference on Neural Networks, IJCNN'05, vol. 2, pp. 815-820 (2005).

Andres-Toro, et al.: "Application of Genetic Algorithms and Simulations for the Optimization of Batch Fermentation Control," IEEE, pp. 392-297 (1997).

Zagonel, G. F. et al: "Multivariate Monitoring of Soybean Oil Ethanolysis by FTIR"; TALANTA, [Online] vol. 63, No. 4 Jul. 8, 2004, pp. 1021-1025, XP002475272; ISSN: 0039-9140 URL:http://www.sciencedirect.com/science/article/B6TH-4BYC4WP-3/2/61e114baa2783edf55610a541e1a626> [retrieved on Apr. 7, 2008] p. 1021-p. 1025.

* cited by examiner

INTEGRATED MODEL PREDICTIVE CONTROL OF BATCH AND CONTINUOUS PROCESSES IN A BIOFUEL PRODUCTION PROCESS

PRIORITY DATA

This application claims benefit of priority of U.S. Provisional Application Ser. No. 60/863,759 titled "Model Predictive Control of a Biofuel Production Process" filed Oct. 31, 2006, whose inventors were Michael E. Tay, Maina A. Macharia, Celso Axelrud, and James Bartee.

This application also claims benefit of priority to U.S. Provisional Application Ser. No. 60/917,916 titled "Nonlinear Model Predictive Control of a Biofuel Fermentation Process" filed May 14, 2007, whose inventors were James F. Bartee and Patrick Noll.

FIELD OF THE INVENTION

The present invention generally relates to the field of model predictive control of production processes for biofuel and its co-products. More particularly, the present invention relates to systems and methods for model predictive control of sub-processes of the biofuel production process and integrated model predictive control of combinations of sub-processes of the biofuel production process, specifically, batch and continuous processes in the biofuel production process.

DESCRIPTION OF THE RELATED ART

History of Biofuel

Biofuel refers to any fuel derived from biomass, i.e., from recently living organisms or their bi-products. Biofuels were used in automobiles from approximately 1876-1908. The Otto Cycle (1876) was the first combustion engine designed to use alcohol and gasoline. Henry Ford's Model T (1908) was designed to use biofuel, gasoline, or any combination of the two fuels. However, high government tariffs on alcohol discouraged the use of biofuel, and gasoline became the predominant fuel choice for automobiles for many decades.

The energy crisis of the 1970s renewed the search for an alternative to fossil fuels. The Energy Tax Act of 1978 (H.R. 5263) provided a 4 cents/gallon exemption from Federal excise taxes to motor fuels blended with biofuel (minimum 10 percent biofuel) and granted a 10% energy investment tax credit for biomass-biofuel conversion equipment (in addition to the 10% investment tax credit available) that encouraged plant building. However, by 1985, only 45% of the 163 existing commercial biofuel plants were operational. This high plant failure rate was partially the result of poor business judgment and inefficient engineering design. In 1988, biofuel was used as an oxygenate in Denver, Colo., which mandated the use of oxygenated fuels during winter use. Oxygenated fuels have been infused with oxygen to reduce carbon monoxide emissions and NOx emissions created during the burning of the fuel. The Clean Air Act in the 1990s, motivated an additional increase in the use of biofuel as a pollution control additive.

The US Congress passed the Clean Air Act Amendments of 1990, which mandated the use of "reformulated gasoline" containing oxygenates in high-pollution areas. Starting in 1992, MTBE was added to gasoline in higher concentrations in accordance with the Clean Air Act Amendments. Improvements in air quality in many areas has been attributed to the use of gas reformulated with MBTE. However by 2000, Methyl Tertiary Butyl Ether (MTBE)—(a carcinogenic agent) was found to have contaminated groundwater systems, mostly through leaks in underground gasoline storage tanks. In 2004, California and New York banned MTBE, generally replacing it with ethanol. Several other states started switching soon afterward. The 2005 Energy Bill required a phase out of MTBE and did not provide legal protection for the oil companies. As a result, the oil companies began to replace MTBE with ethanol (one embodiment of a bio-fuel), thereby spurring growth in the biofuels industry.

Since 2001, there has been a steady rise in crude oil prices that has increased the price of gasoline above the break-even point of biofuel's cost of production. This has been very beneficial to Mid-west agricultural regions that have always sought ways to diversify demand for agricultural goods and services. Biofuel plants that had depended on subsidies to be profitable are now an economically viable venture for this corn-rich region.

Biofuel Production Plants

An exemplary high-level design of a biofuel production plant or process is shown in FIG. 1, which illustrates how biomass is processed through several stages to produce biofuel and one or more co-products. As may be seen, first, biomass is provided to a milling and cooking process, where biomass is broken down to increase the surface area to volume ratio. This increase in surface area allows for sufficient interaction of the fresh water (FW) and biomass surface area to achieve a solution of fermentable sugars in water. The mixture, a biomass/water slurry, may then be cooked to promote an increase in the amount of biomass-water contact in solution and to increase the separation of carbohydrate biomass from the non-carbohydrate biomass. The output of the milling and cooking units (i.e., the fermentation feed or slurry) is then sent to a fermentation process, where one or more fermentation units operate to ferment the biomass/water slurry produced by the milling and cooking process.

The fermentation process may or may not require addition of additional fresh water to the process to control the consistency of material to the fermentation units (also referred to herein as a fermenter). In the fermentation units, biomass is converted by yeast and enzymes into a biofuel, and by-products such as carbon-dioxide, water and non-fermentable biomass (solids).

The output from the fermentation process is sent to a distillation process, e.g., one or more distillation units, to separate biofuel from water, carbon dioxide, and non-fermentable solids. If the biofuel has to be dehydrated to moisture levels less than 5% by volume, the bio-fuel can be processed through a processing unit called a molecular sieve. The finalized biofuel is then processed to ensure it is denatured and not used for human-consumption.

The distillation units separate the biofuel from water. Fresh water (FW) is added in the form of steam for heat and separation, and the condensed water is recycled (RW1) back to the milling and cooking units as shown in FIG. 1. Stillage (non-fermentable solids and yeast residue), the heaviest output of the distillation units, is sent to stillage processing for further development of co-products from the biofuel production process.

Stillage processing units separate additional water from the cake solids and recycle this water (RW2) back to the milling and cooking units. There are a number of stillage processing options: stillage can be sold with minimal processing, or further processed by separating moisture from the solids product via one or more centrifuge units. From the centrifuge the non-fermentable solids are transported to dryers for further moisture removal. A portion of the stillage liquid may be recycled back to the fermentation units; however, the bulk of the flow is generally sent to evaporator units, where more liquid is separated form the liquid stream, causing the liquid stream to concentrate into syrup, while solid stillage is sent to an evaporation process, e.g., using a drying unit or evaporator, to dry the solid stillage to a specified water content. The syrup is then sent to the syrup tank. Syrup in inventory can be processed with a number of options: it can be sprayed in the dryer to a specified color or moisture; it can be added to the partially dried stillage product, or it can be is sold as a liquid product. The evaporator unit may have a water by-product stream that is recycled back to the front end (RW2), e.g., to the milling and cooking units.

Note that an energy center supplies energy to various of the processing units, e.g., the milling and cooking unit, the distillation and mole-sieve units, and the stillage processing units. The energy center may constitute a thermal oxidizer unit & heat recovery steam generator that destroys VOC and provides steam to the evaporators, distillation, cook system and dehydration units; it is typically the largest source of heat in the bio-fuels plant In prior art biofuels plants, properties such as temperature or product quality are controlled with traditional control schemes.

Systems can be open or closed. An open loop system is a system that responds to an input, but the system is not modified because of the behavior of the output (see FIG. 2). Open loop systems are only defined by the inputs and the inherent characteristics of the system or process. In the biofuel production process, the system can be the entire bio-processing plant, one process section of the bio-processing plant, such as the milling and cooking units, or control of a variable in a process such as the temperature of the cooking units. For example, in a biofuel system, a reciprocating pump will operate and move a fixed volume of syrup at a rate independent of the upstream and downstream pressures if the pump does not have a pressure control system.

In a closed loop system, the inputs are adjusted to compensate for changes in the output (see FIG. 3), where, for example, these changes may be a deviation from the desired or targeted measurements. The closed loop system senses the change and provides a feedback signal to the process input. Process units in the biofuel system may be closed loop systems if they need to be regulated subject to constraints such as product quality, energy costs, or process unit capacity.

Modern plants apply traditional and advanced controls to regulate complex processes to achieve a specific control objective. Traditional PID controllers and other control systems such as ratio controls, feed-forward controls, and process models may be used to control biofuel production processes (a PID is a control algorithm or device that uses three basic feedback control modes to act on a deviation from its control objective: proportional action control (P), integral action (I), and derivative (D) rate of change action). A DCS (distributed control system) will have many traditional control schemes set up to control the process unit variables at the local control level.

Most biofuel production facilities mill or steep corn, other grains, or other biomass (e.g. sugarcane), and mix this milled carbohydrate base with recycled and fresh waters from a variety of sources and quality.

It is a difficult operating challenge to provide a steady quality and concentration of feed to the fermentation units, and to control fermentation conditions for reliable results. However, due to variability in feed amount, flow rates, mill rates, steep efficiencies, or biomass (e.g., grain) quality, the fermentation output varies dramatically and the process operates sub-optimally due to this large variability. Fermentation end concentrations of biofuel may vary plus or minus 10% or more.

Plants are currently implemented to provide some information to plant operators that enables them to increase or decrease the feed of fermentable sugar and starch concentrations to fermentation tanks. Plant operators monitor the target feed quality and percent solids in the fermentation feed and run the plants to achieve a target percent solids so that each fermentation batch is started with a rough approximation of the target percent solids and each fermentation process runs over a specific time period in an attempt to achieve an output with approximately the design target percent of biofuel. In addition, a recycle flow rate is typically managed to maintain tank inventory levels within safe operating limits, while providing sufficient water/liquid to mix with grain or other biomass solids to fill a fermentation tank within a targeted time period (i.e. fill a vessel of 180,000 gallons in 15 hours so that the fill rate would be 600 gallons per minute).

In addition, levels of various water sources tend to increase or decrease, and operators or level controllers may adjust flows to regain targeted levels. In general, these applications are controlled with flow, level or mill speed controllers (e.g., regulatory level controllers). Some applications of ratio controllers are used in current control systems (e.g., to monitor the ratio of enzyme flow rates to grain slurry flow rates).

Two additional calculated parameters are also important to plant operators. The first parameter is percent recycle (also referred to as backset), which is the fractional percentage of recycled thin stillage (fermentation liquor output from a centrifuge that separates out cattle feed solids). Percent recycle is managed manually to maintain both a rough thin stillage inventory and to operate within a range of fractional percent backset. It is important to manage the fractional percent backset, because the fermentation liquor contains both residual yeast nutrients along with yeast waste products from previous fermentation. Too little or too much backset can be a problem for fermentation productivity.

The second parameter is fermentation inventory, which is a totalized inventory across the filling, draining and fermenting fermentation vessels and key auxiliary equipment. If this total inventory level is held within an acceptably stable band, the front plant section, i.e., the cooking/milling, and fermentation processes, can be managed to match the back plant section, i.e., the distillation and stillage processes, across all batch sequentially operated fermentation vessels. If totalized batch volume is constant, then filling is balanced with draining across multiple parallel batch fermentation vessels.

A biofuel production plant may require numerous adjustments, e.g., on a minute-to-minute basis, in response to changes and shifting constraints if the plant process is to operate in an optimal manner. Due to this complexity, human operators are not capable of actively optimizing a biofuel production process. Consequently, operators generally operate a plant in a comfortable, less efficient operating mode.

Thus, improved systems and methods for biofuel production are desired.

SUMMARY OF THE INVENTION

Various embodiments of a computer-implemented method for integrated control of batch and continuous processes in a biofuel production process utilizing model predictive control (MPC) are presented.

An integrated dynamic multivariate predictive model may be provided that includes at least one continuous process model representing at least one continuous process of the biofuel production process, at least one batch process model representing at least one batch process of the biofuel production process, and a continuous simulation framework. The at least one batch process model may interact with the at least one continuous process model as an equivalent virtual nonlinear continuous process via the continuous simulation framework using one or more bridging equations. In other words, as described above, the continuous simulation framework may facilitate integrated modeling of the at least one batch process and the at least one continuous process by allowing the at least one batch process model to interact or interface with the at least one continuous process model in such a way that the at least one batch process model represents the at least one batch process as a virtual continuous process. Said another way, the at least one batch process may be represented to the at least one continuous process model as a virtual continuous process, thus facilitating interactions between the at least one batch process model and the at least one continuous process model in continuous process terms.

Note that, as discussed above, in some embodiments, the at least one batch process model models the at least one batch process as the nonlinear continuous process using the one or more bridging equations. In other words, the at least one batch process model may use the bridging equations or transforms to model the at least one batch process as one or more continuous processes. Thus, in some embodiments, the framework may be part of the at least one batch process model.

In an alternative embodiment, the at least one batch process model may interact with the at least one continuous process model through the one or more bridging equations, where the one or more bridging equations include transforms that translate batch parameters to continuous parameters. This may allow the at least one batch process model and the at least one continuous process model to respond simultaneously to the process information, i.e., may allow the models to operate on a common ground. Thus, in some embodiments, the framework may operate as a translation interface for the at least one batch process model, allowing it to appear to or interact with the at least one continuous process as a continuous process model itself.

In other words, in both of these approaches, the framework allows both models to respond to process information in common terms, specifically, in continuous process terms, despite the batch nature of the at least one batch process.

In some embodiments, the at least one batch process may include or be a batch fermentation process for the biofuel production process, which, as described above, processes the fermentation mash or slurry in batches (in one or more fermentation vats or tanks). The at least one continuous process may include one or more continuous process of the biofuel production process, such as, but not limited to: a cooking and milling process (i.e., the fermentation feed, including upstream sources), a distillation and dehydration process, and/or a stillage process, among others.

An objective for the biofuel production process may be received, e.g., specifying or encoding a desired behavior or outcome of the biofuel production process. In some embodiments, the objective may be complex or compound. For example, the objective may include a global objective, and a plurality of sub-objectives directed to at least a subset of the plurality of sub-processes, including the at least one batch process and the at least one continuous process. Said another way, the objective may include an overall objective for the biofuel production process, e.g., maximize throughput, efficiency, etc., and may also include various subsidiary objectives related specifically to the respective sub-processes, or combinations of sub-processes. Note that these sub-objectives may in some cases be mutually exclusive or competitive with respect to one another and/or with respect to the global objective. Additional sub-objectives related to other, e.g., secondary, goals of the production process may also be included in the objective as desired.

Exemplary objectives may include, but are not limited to, one or more operator specified objectives, one or more predictive model specified objectives, one or more programmable objectives, one or more target feed rates, one or more cost objectives, one or more quality objectives, one or more equipment maintenance objectives, one or more equipment repair objectives, one or more equipment replacement objectives, one or more economic objectives, a target throughput for the biofuel production process, one or more objectives in response to emergency occurrences, one or more dynamic changes in materials inventory information, and/or one or more dynamic changes in one or more constraints on the biofuels production process, among others.

Constraint information specifying one or more constraints for the biofuel production process i.e., limitations on one or more aspects or variables of the biofuel production process, may be received, where in preferred embodiments, the one or more constraints are in terms of the continuous simulation framework. For example, the constraints may be in terms of continuous process parameters or variables, including, for example, virtual continuous parameters use to model or represent, or communicate with, the batch process as a continuous process, as described above.

Process information related to the plurality of sub-processes, including process information for the at least one batch process, and the at least one continuous process, may be received from the biofuel production process. This process information may be any type of process information, including state or condition information measured by sensors, (e.g., temperatures, pressures, real-time measurements of the biofuel in the fermentation system), computed algorithmically, inferred from models (i.e., inferential models), and/or lab values, and/or entered by operators, among others. This process information may further include equipment settings, flow rates, material properties, such as densities, content profiles, purity levels, ambient conditions, such as time of day, temperature, pressure, humidity, etc., economic or market conditions, such as cost of materials or product, and so forth. In other words, the process information may include any information that affects or influences any part of the biofuel production process.

The integrated dynamic multivariate predictive model may be executed in accordance with the objective using the received process information as input, to generate model output comprising target values for one or more variables related to the at least one batch process and the at least one continuous process in accordance with the objective and subject to the one or more constraints. In other words, the model may execute to determine target values for manipulated variables for the at least one batch process and the at least one continuous process that may be used to control the sub-processes in such a way as to attempt to meet the objective.

The plurality of sub-processes of the biofuel production process, including the at least one batch process and the at least one continuous process of the biofuel production process, may be controlled in accordance with the target values and the objective, subject to the one or more constraints. In other words, a controller (or a plurality of controllers) may modulate or otherwise control various operational aspects of the sub-processes in accordance with the target values of the manipulated variables, attempting to meet the objective, subject to the constraints. In some embodiments, the target values may simply be used as set points by the controller, i.e., the controller may set respective inputs of the various sub-processes to the respective target values. For example, controlling the plurality of sub-processes of the biofuel production process in accordance with the target values and the objective may include operating one or more controllers to control one or more of: one or more material feed rates, one or more water flows, one or more molecular sieve regenerations, one or more heat sources, and so forth, including any controllable aspects of the sub-processes useable to pursue and possibly meet the objective (or objectives).

The above receiving the objective, receiving process information, executing the integrated dynamic multivariate predictive model, and controlling, may be performed a plurality of times in an iterative manner to operate the biofuel production process in a substantially optimal fashion. In other words, the method described herein may be performed substantially continuously, i.e., at some specified frequency or in response to a schedule or events, providing online control of the biofuel production process in substantially real time to optimize the biofuel production process (with respect to the objective). In some embodiments, the constraint information may also be received iteratively, particularly in the case of dynamic constraints.

In some embodiments, executing the dynamic multivariate predictive model includes an optimizer executing the dynamic multivariate predictive model in accordance with the objective using the received process information and the one or more constraints as input, thereby generating the model output in accordance with the objective and subject to the one or more constraints. For example, in one embodiment, the optimizer may execute the dynamic multivariate predictive model a plurality of times in an iterative manner. In embodiments where multiple objectives are provided, possibly at odds with one another, an optimizer may be used to balance the various sub-objectives in attempting to meet the global objective. In other words, an optimizer may be used to determine what, where, and when to compromise with respect to various of the sub-objectives in attempting to achieve or at least approach the global objective. Thus, in some embodiments, executing the dynamic multivariate predictive model may include an optimizer executing the dynamic multivariate predictive model to generate the model output, including the target values of one or more variables related to the at least one batch process and the at least one continuous process, in accordance with the global objective, and at least partially in accordance with the plurality of sub-objectives.

For example, the optimizer may repeatedly execute the model under various inputs and compare the resulting outputs to the objective (including the sub-objectives), thereby searching the solution space for input configurations that optimize the outcome, e.g., that allow the global objective to be met or at least approached, while minimizing the compromises made with respect to the various sub-objectives.

Thus, various embodiments of the systems and methods described herein may be used to substantially optimize biofuel production in a biofuel production process.

BRIEF DESCRIPTION OF THE DRAWINGS

A better understanding of the present invention can be obtained when the following detailed description of the preferred embodiment is considered in conjunction with the following drawings, in which.

Figure 1:
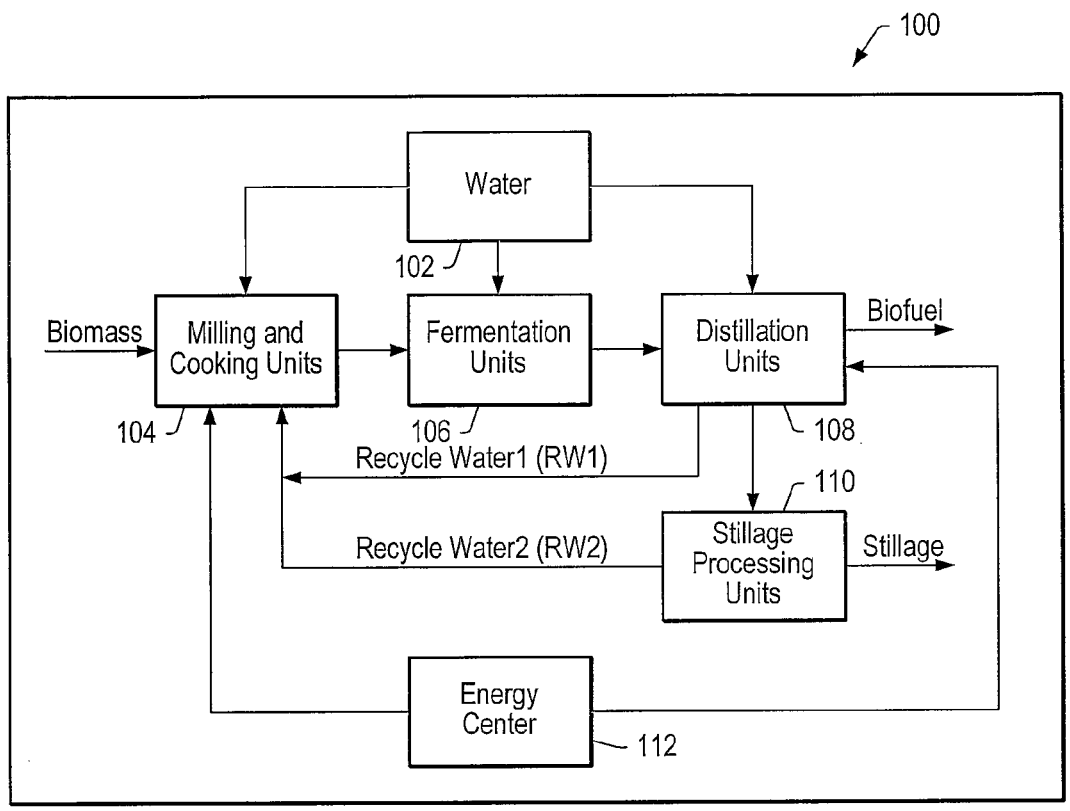
FIG. 1 illustrates a general design of a prior art biofuel processing plant.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION OF THE INVENTION

Incorporation by Reference

The following references are hereby incorporated by reference in their entirety as though fully and completely set forth herein:

U.S. Provisional Application Ser. No. 60/863,759, titled "Model Predictive Control of a Biofuel Production Process", filed Oct. 31, 2006.

U.S. Provisional Application Ser. No. 60/917,916, titled "Nonlinear Model Predictive Control of a Biofuel Fermentation Process", filed May 14, 2007.

U.S. patent application Ser. No. 11/757,557, titled "Model Predictive Control of a Fermentation Feed in Biofuel Production", filed Jun. 4, 2007.

U.S. patent application Ser. No. 11/862,391, titled "Model Predictive Control of Distillation and Dehydration Sub-Processes in a Biofuel Production Process", filed Sep. 27, 2007.

U.S. patent application Ser. No. 11/924,370, titled "Model Predictive Control of Integrated Stillage Processing in a Biofuel Production Process", filed Oct. 25, 2007.

U.S. patent application Ser. No. 11/927,899, titled "Model Predictive Control of Fermentation in Biofuel Production" filed Oct. 30, 2007.

U.S. patent application Ser. No. 11/927,960, titled "Nonlinear Model Predictive Control of a Biofuel Fermentation Process", filed Oct. 30, 2007.

U.S. patent application Ser. No. 11/928,344, titled "Model Predictive Control of Fermentation Temperature in Biofuel Production", filed Oct. 30, 2007.

DEFINITIONS

Biofuel Production Processes

Biofuel—any fuel (or fuels) derived from biomass, i.e., from recently living organisms or their bi-products.

Biofuel production process—a fermentation process surrounded by auxiliary processing units to produce biofuel, other fermentable alcohols for fuel, and high-capacity food grade or chemical grade alcohols.

Biofuel production—a measure of biofuel production within or at the end of a batch process. May include measurements such as concentration (e.g., wt %, volume % or wt/vol %), volume (e.g., current gallons biofuel within a fermenter) or mass (e.g., current kg biofuel within a fermenter).

Batch processing—a staged discontinuous processing step that includes a start and an end, in contrast to continuous processing that continues without stop, e.g., during a normal operating day or week. Continuous processing is generally represented by fairly steady targets or operations, where at least some parameters change throughout batch processing. For example, biofuel production, e.g., fermentation, starts at low levels at the start of a batch and increases throughout the batch with or without a drop at the end representing degradation rates being higher than production rates. Similarly, yeast cellular concentrations, start at fairly low levels, and generally grow throughout a batch, although they generally have a lag (relatively constant concentrations), exponential growth, stable growth and degradation phase within a batch.

Slurry—a fermentation feed mash comprising a two-phase (liquid and solid) slurry that will be fermented.

Solids or % solids—fraction or percent of solids in the fermentation feed.

Milling and Cooking Process—continuous processing for pre-fermentation of the fermentation feed, which generally includes grain or cane milling, cooking, mixing with water and processing chemicals, cooking for sterilization and increasing water concentration within solids, and other pre-fermentation processing.

Biomass concentration—content attribute of the fermentation feed specified by one or more of: slurry solids, liquefaction solids, slurry density, liquefaction density, slurry % or fraction carbohydrates, and slurry % or fraction fermentable sugar.

Water inventory information—includes water flows, recycle liquid flows, evaporator condensate recycle flow, thin stillage or centrifuge liquor recycle flows, fresh water addition flows, processed water addition flows, slurry flows, mash flows, and various levels or weights for various tanks used to hold inventories of these flows or for intermediate receptacles (e.g. methanator feed tank, slurry feed tank, liquefaction tank, distillate tank, grain silo inventories or other biomass inventories (not water) etc.).

Liquefaction—for grains with high starch content, the starch is liquefied to reduce its carbohydrate chain length and viscosity by adding enzymes or other biologic agents.

Thermal Oxidizer/Heat Recovery Steam Generator (HRSG)—process equipment that is used to destroy volatile organic compounds (VOCs), to reduce air and remove stenches from stillage dryer or evaporation systems. The heat recovery steam generator is used to recover the heat required to destroy the VOCs, and is typically the energy center of the biofuels production process.

Dried Distillers Grains (DDG)—post fermentation solid residue that includes undigested grain residue, other solid residues (enzymes, salts), and yeasts (or other cellular residue) that may be dried and released as a production by-product (generally as animal feed). DDG may also be used herein to include WDG (wet distillers grains), which are only partially dried for local consumption (e.g. without long-term biological stability) and DDGS/WDGS (dried distillers grains with solubles and wet distillers grains with solubles). Solubles includes residue solids that are soluble in water and therefore present in stillage concentrate. Solubles may be partially concentrated (generally with evaporation), and added to DDG or WDG to increase yields and manage by-product inventories.

Enzyme—highly selective biological-based catalyst added to manage specific reactions within a fermentation process. The most common enzymes used today include alpha amylase to rapidly break starches into dextrins, gluco-amylase to break dextrins into glucose, and proteases to break grain proteins into digestible proteins to support cell growth. In the same way as described below, modeling and controlling starch-based fermentations, enzymes specific for cellulosic conversion into biofuels or other enzymes affecting yeast (see below), growth or nutrient availability may be managed.

Yeast—a biofuel producing organism. Yeasts are currently the most commonly used organism in ethanol production although other biofuel producing organisms including genetically engineered *E. coli* can be substituted throughout as the technology described may not be specific to yeast, and may apply to many organisms used in fermentation processes to produce biofuel.

Stillage/Whole Stillage—non-fermentable solids and water liquid removed from the bottom of the primary distillation units.

Thin Stillage—the separated liquid from the stillage non-fermentable solids.

Syrup—concentrated thin-stillage with a large portion of the moisture removed. The % solids in syrup are usually in the range of 20-45% solids, but percentages outside this range may occur.

Azeotrope—a special mixture of two compounds, that when in equilibrium, the vapor phase and liquid phase have exactly the same compositions. This makes it difficult to separate the two components to achieve a better purity. Special separation processes are required to break the azeotrop. They comprise azeotropic distillation (add a $3^{rd}$ compound to break the azeotrop), extractive distillation (use a solvent to separate the 2 compounds), or molecular sieve technology (preferentially trap molecules of one component in a molecular sieve bed as the other component passes over the molecular sieve bed).

Volatile Organic Compounds (VOCS)—Organic compounds that tend to vaporize when subject to atmospheric pressure and ambient temperature ranges.

Capacity—capacity is the established maximum production rate of the process, sub-process, or unit under best operating conditions (no abnormal constraints). Capacity is generally a constant within the present capital investment. For new units it is the vendor's specified capacity. For established units, capacity is established by demonstrated historical production rates.

Model—an input/output representation, which represents the relationships between changes in various model inputs and how the model inputs affect each of the model outputs.

Dynamic Predictive Model—an input/output representation that not only reflects how much an output changes when an input is changed, but with what velocity and over what time-dependent curve an output will change based on one or more input variable changes.

Dynamic Predictive Model—an input/output representation of a system or process that not only reflects how much an output changes when an input is changed, but with what velocity and over what time-dependent curve an output will change based on one or more input variable changes. A dynamic multivariate predictive model is a dynamic predictive model that represents or encodes relationships among multiple parameters, and is operable to receive multiple inputs, and generate multiple outputs.

Model Predictive Control (or MPC)—use of multivariate dynamic process models to relate controller objectives (targeted controller outputs and constraints) with regulatory controllers (existing single-input/single-output controllers such as ratio flow, temperature, level, speed, or pressure controllers) over a predicted time interval (e.g., 1 minute, 30 minutes, 2 hours, 100 hours, etc.).

Objective Function—sets the goals for the overall operation of the process or unit. The objective function provides one or several consistent numerical metric(s) to which the process or unit strives to achieve and over which the performance of the process or unit may be measured, e.g., minimize the cost of operation, or maximize profit or production of the operation.

Control Variables—(also called controlled variables) those variables that the controller/optimizer tries to bring to some objective, e.g., to a target value, maximum, etc.

Integrated Variables—integrated control variables are variables that are not stable, but integrate generally with a stable first derivative as a function of time. The most common integrated variable is a tank level where as long as inputs and outputs are imbalanced the level will increase or decrease. Thus, when balanced a change in an input or output flow will cause a tank to either overfill or drain as integrated over time. A controller must use these integration calculations to determine when and how rapidly input or output flows must be adjusted.

Manipulated Variables—those variables over which the management of the process or unit has authority and control, e.g., via regulation of the process with online controllers, and which are changed or manipulated by the controller/optimizer to achieve the targets or goals of the control variables. These variables are the actual control variables whose values are limited by the constraints. This is in distinction from controllable constraints in the sense that manipulated variables may operate within some range of controllable or fixed constraints. Manage is an alternate term for process control.

Disturbance Variable—a variable representing an external influence on a process that, in addition to objective variables and regulatory controllers, is outside the controller scope, and so it acts on the objective variables, but independently of the described controller. Disturbance variables are used in feed-forward disturbance rejection. Disturbance variables are also measured or unmeasured variables over which the management of the process or unit does not have direct authority or control. For example, temperature, humidity, upstream flow, or quality, may all be referred to as measured disturbance variables.

Set Point (targets)—the target signal or value for a manipulated variable or targeted controlled variable.

Constraints—Constraints represent limitations on particular operating variables or conditions that affect the achievable production rate of a production unit. Constraints are of two types: controllable and external, defined below. Constraints may include, but are not limited to: safety constraints, equipment constraints, equipment availability constraints, personnel constraints, business execution constraints, control constraints, supply chain constraints, environmental permit and legal constraints. Safety constraints ensure the safety of equipment and personnel. Equipment constraints, such as the maximum open position of a control valve, maximum tank capacity, etc., may limit the physical throughput of the unit. Equipment availability constraints may include, but are not limited to: readiness due to maintenance planning and scheduling, or due to unexpected equipment outages, authorized production level set by the supply chain and production scheduling systems. Personnel constraints refer to limitations on the availability of staffing and support functions, business rules and constraints imposed by contract and policy. Business execution constraints are limits imposed by the time required to execute associated business and contractual tasks and obligations. Control constraints are limits on the maximal position and rate of change of manipulated variables. Supply chain constraints are limits on the availability of raw materials, energy, and production supplies. Environmental permit and legal constraints are limits on air emissions, waste water, and waste disposal systems, and/or environmental constraints imposed upon the performance of the unit, such as river levels and current weather imposed limitations.

Controllable Constraints—constraints imposed on the performance of a process or unit over which the management of the process or unit does have authority and discretionary control. For example, the separation in a distillation tower may be affected by distillation tray fouling. The tray fouling is a function of how the feed-stock is processed, and how often the unit is taken offline for clean-up. It is management's discretion as to when the unit is serviced. Controllable constraints change a unit's throughput capacity.

External Constraints—constraints imposed on the performance of the process or unit over which the management of the process or unit does not have authority or discretionary control. These external constraints come in two types: external constraints that are controllable by other entities or processes in the plant or in the supply chain, and those constraints that are imposed by physical, safety, environmental, or legal constraints and are not controllable by anyone in the plant or supply chain.

External Constraints—external constraints are limitations imposed on the performance of the process, sub-process, or unit over which the management of the process, sub-process, or unit does not have authority or discretionary control. These external constraints come in two types: external constraints that are controllable by other entities or processes in the plant or in the supply chain, and those constraints that are imposed by physical, safety, environmental, or legal constraints and are not controllable by anyone in the plant or supply chain.

Objective Function—the objective function encodes an objective that sets the goal or goals for the overall operation of the process, sub-process, or unit. The objective function provides one or more consistent numerical metric(s) to which the process, sub-process, or unit strives to achieve and over which the performance of the process, sub-process, or unit may be measured, e.g., from a business standpoint.

System—a system may be defined by the inputs and the characteristics of the system or process. In the biofuel production process, the system may be defined for: the entire biofuel production process, a sub-process of the biofuel production process such as the milling and cooking process, or a variable in a sub-process such as the cooking temperature.

Figure 2:
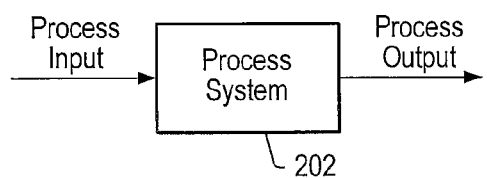
FIG. 2 illustrates a general design of a prior art open loop process system.
Figure 3:
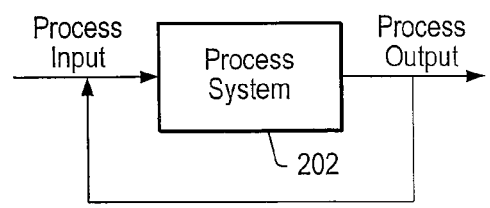
FIG. 3 illustrates a general design of a prior art closed loop process system.

Open Loop Systems—are systems that respond to an input, but the system is not modified because of the behavior of the output (see FIG. 2). For example, in a biofuel system, a reciprocating pump will operate and move at a fixed volume of syrup independent of the upstream and downstream pressure if the reciprocating pump does not have a pressure control system.

Closed Loop Systems—system inputs may be adjusted to compensate for changes in the output. These changes may be a deviation from an objective for the system, impacts of constraints on the system or system variables, or measurements of output variables. The closed loop system may be used to sense the change and feedback the signal to the process input. In biofuel systems, closed loop systems may predominate, since these systems may be regulated subject to constraints such as production (product) quality, energy costs, process unit capacity, etc.

Control Variables—Control variables (also called controlled variables) are those variables that the controller/optimizer tries to bring to some objective, e.g., to a target value, maximum, etc.

Manipulated Variables—Manipulated variables are those variables over which the management of the process or unit has authority and control, and which are moved or manipulated by the controller/optimizer to achieve the targets or goals of the control variables. These variables are the actual control variables whose settings are limited by the constraints. This is in distinction from controllable constraints in the sense that manipulated variables may operate within some range of controllable or fixed constraints.

Set Point (Targets)—The set point is the target signal or value for a manipulated variable.

Disturbance Variables—Disturbance variables are measured or unmeasured variables over which the management of the process or unit does not have direct authority or control. For example, temperature, humidity, upstream flow or quality, may all be referred to as measured disturbance variables.

Control System—the regulatory level mechanism by which the manipulated variables are driven to the set points.

Response—the measurement of the current position of the manipulated variable. The response is the feedback of the movement of the manipulated variable to the set point in response to the actions of the control system in its effort to achieve the set point.

Target Profile—a desired profile or trajectory of variable values, i.e., a desired behavior of a control variable or a manipulated variable.

Control Horizon—the period of the time extending from the present into the future during which one plans to move or change manipulated variables. Beyond this horizon the MV is assumed to stay constant at its last or most recent value in the control horizon.

Prediction Horizon—the period of time extending from the present into the future during which the process or system response is monitored and compared to a desired behavior.
MPC Applied to a Sub-Process of a Biofuel Production Process Below are described various embodiments of systems and methods for applying model predictive control to a biofuel production process. In this approach to biofuel production, a dynamic multivariate predictive model may be incorporated as a process model in a dynamic predictive model-based controller. This MPC system may project or predict what will happen in the production process (e.g., in the near future) based on the dynamic prediction model and recent process history, including, for example, recent operating conditions or state values. This projection or prediction may be updated or biased based on received current process information, and control algorithms may be used to recursively estimate the best current and future control moves on the model inputs to achieve a desired output path. Targets set on the dynamic model outputs may be compared to how that output may behave over a predictive future horizon and the best available controllable model input moves may be estimated to best achieve the controller targets.

It should be noted that the biofuel or biofuels produced by embodiments of the methods described herein may be any of biofuel generated from biomass, and that the types of biomass contemplated may be of any type desired, including, but not limited to, grains, such as corn, wheat, rye, rice, etc., vegetables, e.g., potatoes, beats, etc., canes, such as sugarcane, sorghum, and so forth, among others.

Figure 4:
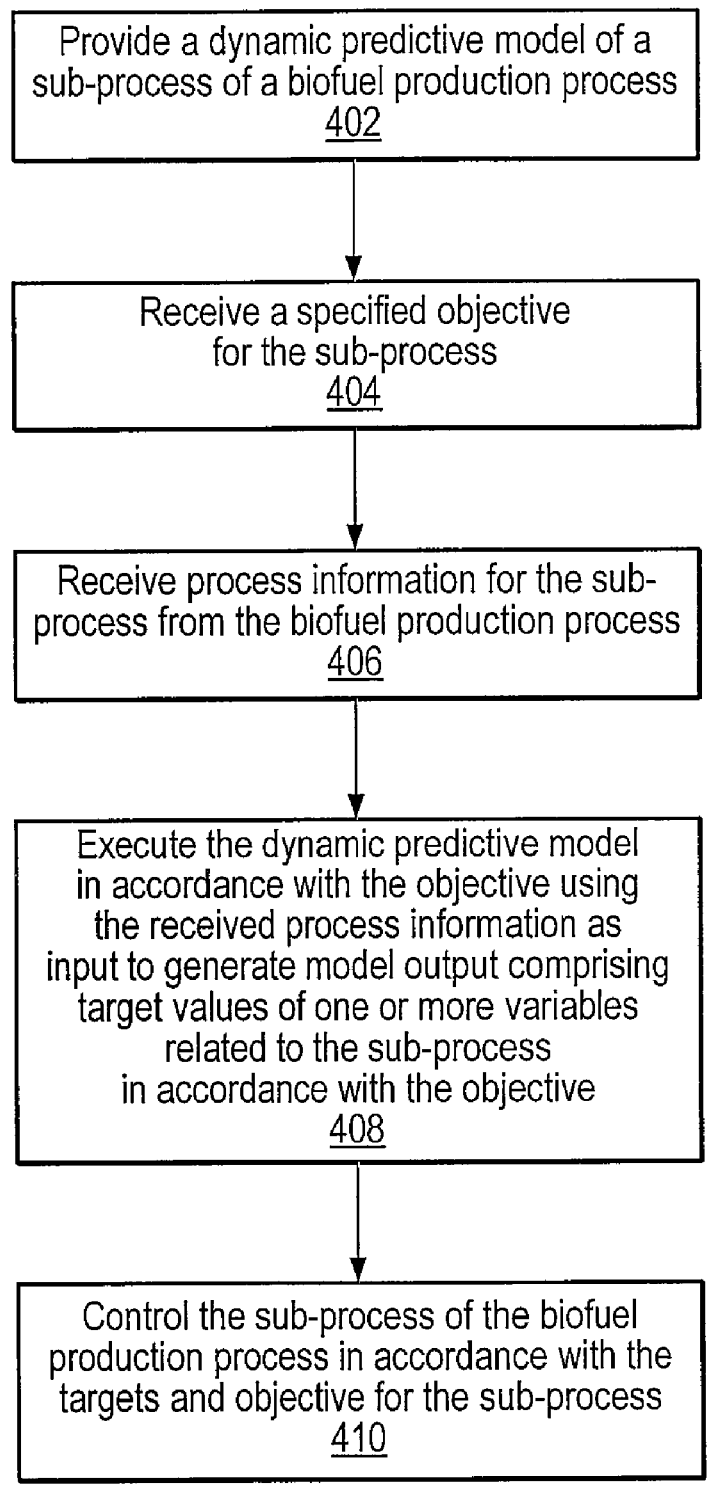
FIG. 4 is a high-level flowchart of a method for managing a sub-process of a biofuel production process utilizing model predictive control, according to one embodiment.

FIG. 4 is a high-level flowchart of a computer-implemented method for managing a sub-process of a biofuel production process utilizing model predictive control (MPC), according to one embodiment. As used herein, the term biofuel refers to one or more biofuel products output from a biofuel production process. It should be noted that embodiments of the method of FIG. 4 may be used with respect to any sub-process of a biofuel production process desired, e.g., cooking/milling, fermentation feed management, fermentation, distillation, and stillage processing, among others, as will be described in more detail below. In various embodiments, some of the method elements shown may be performed concurrently, in a different order than shown, or may be omitted. Additional method elements may also be performed as desired. As shown, this method may operate as follows.

In 402, a dynamic multivariate predictive model of a sub-process of a biofuel production process may be provided. In other words, a model may be provided that specifies or represents relationships between attributes or variables related to the sub-process, including relationships between inputs to the sub-process and resulting outputs of the sub-process. Note that the model variables may also include aspects or attributes of other sub-processes that have bearing on or that influence operations of the sub-process.

The model may be of any of a variety of types. For example, the model may be linear or nonlinear, although for most complex processes, a nonlinear model may be preferred. Other model types contemplated include fundamental or analytical models, i.e., functional physics-based models, empirical models, such as neural networks or support vector machines, rule-based models, statistical models, standard MPC models, i.e., fitted models generated by functional fit of data, and/or hybrid models using any combination of the above models.

In 404, an objective for the sub-process may be received. The objective may specify a desired outcome, result, behavior, or state, of the sub-process, such as, for example, a desired throughput, quality, efficiency, product profile, behavior, or cost, among others. In preferred embodiments, the objective may specify at least one targeted measurable attribute defining product quality for the sub-process (or the overall production process). Note that an objective may be a specific value, such as a specified percent solids for a fermentation feed, a specified temperature of a fermentation vat, etc., or may be a specified extremum, i.e., a maximum or minimum of an attribute, such as, for example, minimizing cost, maximizing production, etc. Moreover, in some embodiments, an objective may include multiple components, i.e., may actually comprise a plurality of (sub-)objectives. In other words, in some embodiments, the objective may involve multiple variables. Moreover, in some embodiments, there may be a global objective, e.g., maximize production or profit, and multiple sub-objectives that may in some cases be at odds with the global objective and/or one another. In various embodiments, the objective for the fermentation feed may specified by a human operator, and/or a program, i.e., manually and/or programmatically.

In 406, processing information for the sub-process of the biofuel production process may be received. In other words, information related to the sub-process may be received from the sub-process (or from other portions of the biofuel production process that influence the sub-process). This information generally includes data from one or more sensors monitoring conditions of and in the sub-process, e.g., temperatures, pressures, flow rates, equipment settings, and so forth, although any other information germane to the sub-process may be included as desired, e.g., constraints to which the sub-process may be subject, ambient conditions of the biofuel process, economic or market data, and so forth.

In 408, the model may be executed in accordance with the objective for the sub-process using the received processing information as input, thereby generating model output comprising target values for one or more manipulated variables related to the sub-process in accordance with the objective for the sub-process. In other words, the model may be executed with the received processing information as input, and may determine target values of one or more controllable attributes of the sub-process in an attempt to meet the specified objective for the sub-process (which could be a global objective for the entire biofuel production process). For example, in an embodiment where the objective is to maximize output for the sub-process, the model may determine various target values, e.g., sub-process material input flows, temperatures, pressures, and so forth, that may operate to maximize the output.

In 410, the sub-process of the biofuel production process may be controlled in accordance with the corresponding targets and objective for the sub-process. Said another way, a controller coupled to the dynamic multivariate predictive model may automatically control various (controllable) aspects or variables of the sub-process according to the target values output by the predictive model to attempt to achieve the specified objective.

Figure 5:
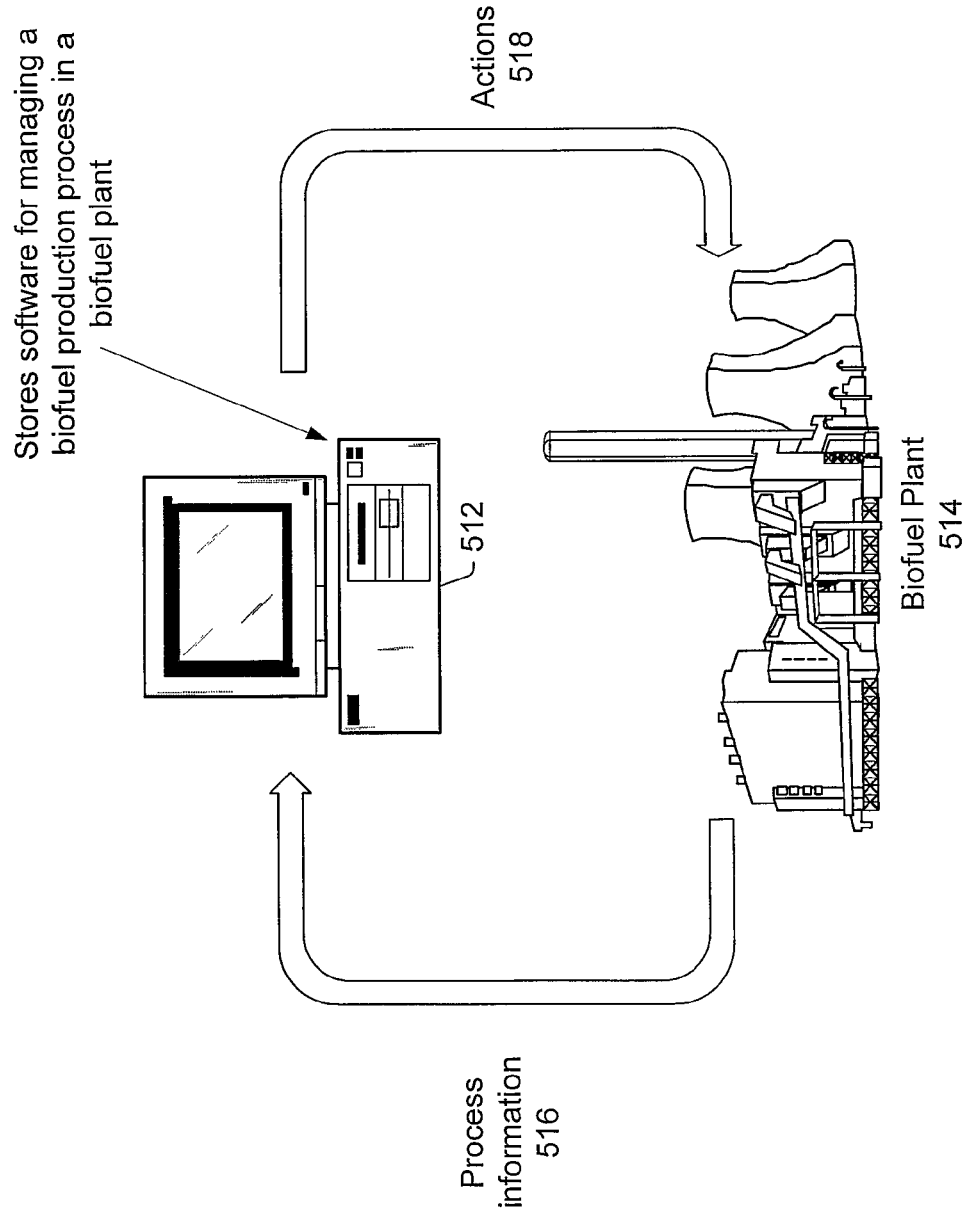
FIG. 5 is a simplified view a system for performing model predictive control of a biofuel production process, according to one embodiment.

FIG. 5 illustrates a simplified view of an automated control system for a biofuel production plant 514. As shown, the system may include one or more computer systems 512 which interact with the biofuel plant 514 being controlled. The computer system 512 may represent any of various types of computer systems or networks of computer systems which execute software program(s) according to various embodiments of the invention. As indicated, the computer system stores (and executes) software for managing fermentation in the biofuel plant 514. The software program(s) may perform various aspects of modeling, prediction, optimization and/or control of the fermentation process. Thus, the automated control system may implement predictive model control of fermentation and/or other processes or sub-processes in the biofuel plant or process. The system may further provide an environment for making optimal decisions using an optimization solver, i.e., an optimizer, and carrying out those decisions, e.g., to control the plant.

One or more software programs that perform modeling, prediction, optimization and/or control of the plant 514 (e.g., batch fermentation in conjunction with one or more continuous processes) may be included in the computer system 512. Thus, the system may provide an environment for a scheduling process of programmatically retrieving process information 516 relevant to the processes of the plant, and generating actions 518, e.g., control actions, to control the fermentation process, and one or more continuous processes of the biofuel plant or process.

The one or more computer systems 512 preferably include a memory medium on which computer programs according to the present invention are stored. The term "memory medium" is intended to include various types of memory or storage, including an installation medium, e.g., a CD-ROM, or floppy disks, one or more computer system memories or random access memory such as DRAM, SRAM, EDO RAM, Rambus RAM, etc., or a non-volatile memory such as a magnetic medium, e.g., a hard drive, or optical storage. The memory medium may comprise other types of memory as well, or combinations thereof. In addition, the memory medium may be located in a first computer in which the programs are executed, or may be located in a second different computer which connects to the first computer over a network. In the latter instance, the second computer provides the program instructions to the first computer for execution. The memory medium may include a plurality of memory media, possibly distributed across multiple computer systems.

Also, the computer system(s) 512 may take various forms, including a personal computer system, mainframe computer system, workstation, network appliance, Internet appliance or other device. In general, the term "computer system" can be broadly defined to encompass any device (or collection of devices) having a processor (or processors) which executes instructions from a memory medium.

The memory medium (which may include a plurality of memory media) preferably stores one or more software programs for performing various aspects of model predictive control and optimization. The software program(s) are preferably implemented using component-based techniques and/or object-oriented techniques. For example, the software program may be implemented using ActiveX controls, C++ objects, Java objects, Microsoft Foundation Classes (MFC), or other technologies or methodologies, as desired. The software programs may include one or more nonlinear models, e.g., artificial neural networks, support vector machines, etc., as desired. A CPU, such as the host CPU, executing code and data from the memory medium comprises a means for creating and executing the software program according to the methods or flowcharts described below. In some embodiments, the one or more computer systems may implement one or more controllers, as noted above.

Figure 6:
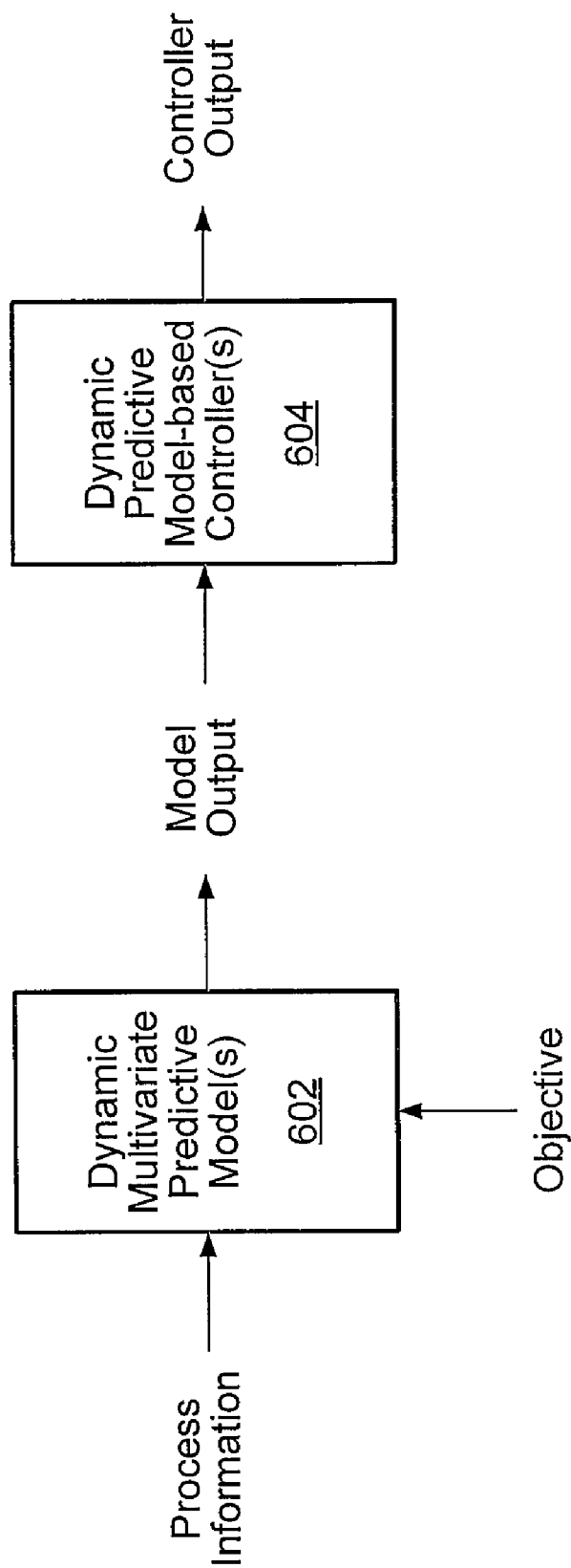
FIG. 6 illustrates model predictive control of sub-processes of a biofuel production process, according to one embodiment.

FIG. 6 illustrates an exemplary system for managing a sub-process of a biofuel production process, which may implement embodiments of the method of FIG. 4. The system may comprise: 1) at least one dynamic multivariate predictive model 602 (e.g., at least one predictive control model) of each sub-process in the biofuel production process to be controlled; and 2) a dynamic predictive model-based controller 604 coupled to the dynamic multivariate predictive model(s). As described above with respect to FIG. 4 in more detail, the dynamic multivariate predictive model may be executable to: receive an objective for a sub-process, receive processing information for the sub-process of the biofuel production process, execute the model in accordance with the objective for the sub-process using the received corresponding processing information as input, thereby generating model output comprising targets for one or more variables related to the sub-process in accordance with the objective for the sub-process, and may control the sub-process of the biofuel production process in accordance with the corresponding targets and objective for the sub-process.

The following describes various examples of model predictive control of one or more sub-processes of a biofuel production process according to the method of FIG. 4. Note, however, that the particular sub-processes described are meant to be exemplary, and that such model predictive control may be applied to any other sub-processes of the biofuel production process as desired.

Integrated Model Predictive Control of a Biofuel Production Process

Above were described various systems and methods for applying model predictive control (MPC) to sub-processes in a biofuel production process or plant, e.g., fermentation feed, fermentation, distillation, and stillage. As described in detail above with reference to FIG. 1, each of these sub-processes may operate within a larger biofuel production process to convert biomass to biofuel and possibly one or more co-products. Thus, the biofuels plant may typically include four plant sections: milling/cook, fermentation, distillation/sieves, and stillage processing. Each of these sections may be at least partially dependent upon operation of one or more of the other sections. Moreover, operating conditions that may be optimal for one sub-process or section may entail or cause inefficiencies in one or more of the other sub-processes or sections. Thus, a plant bottleneck, meaning a local limitation that limits or restricts a global process, can occur in any of the above four sub-processes, thus limiting the overall operation of the biofuel production process.

Figure 7A:
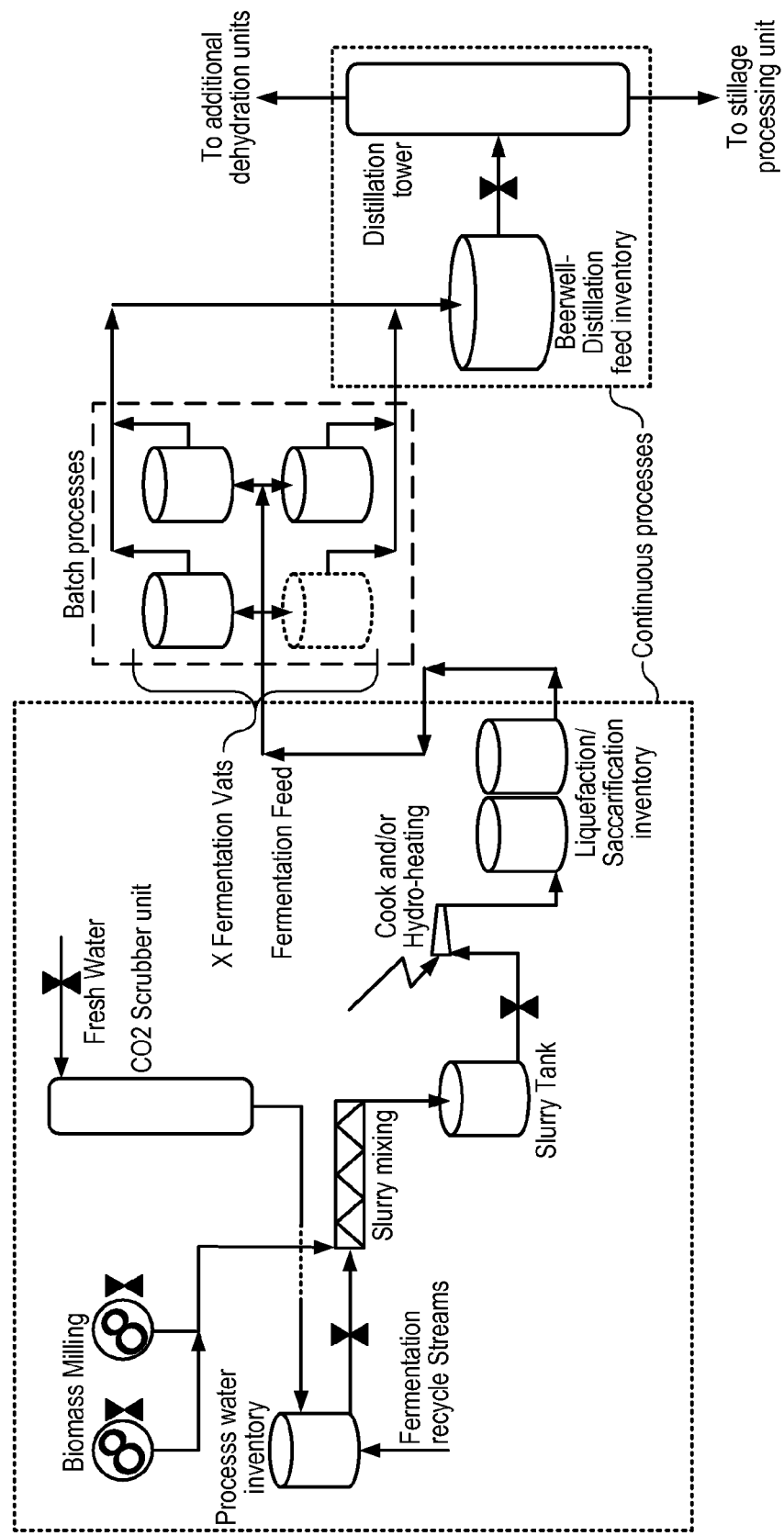
FIG. 7A illustrates batch and continuous processes in a biofuel production process, according to one embodiment.

The biofuel production process can be viewed as an integration of batch and continuous processes. For example, FIG. 7A illustrates batch and continuous processes in a biofuel production plant. As may be seen, the fermentation process is a batch process, where one or more fermentation vats, referred to as fermenters, are operated (e.g., in parallel) to ferment successive batches of biomass/water slurry to generate biofuel. The batch fermentation (including, for example, fermentation cycle time and solids concentration) is typically adjusted to operate the entire plant, possibly subject to one or more active process constraints. Other processes of the biofuel production process, i.e., sub-processes, are continuous processes, i.e., are processes in which a substantially continuous stream of material is processed or operated on, with substantially continuous input and output of the process. Examples of continuous (sub-)processes in the biofuel production process include, but are not limited to, cooking and milling, distillation and dehydration, and stillage processes. Each of these sub-processes may have respective objectives and constraints particular to that sub-process, possibly in conflict or competition with one another. Moreover, due to the substantial differences between batch processing and continuous processing, objectives for these two types of processes are often at odds with one another.

In prior art approaches, the control of these sub-processes is performed manually, e.g., based on decisions of a human operator, or is only locally automated, e.g., via PID inventory controls of fermentation inventory and fermentation feed inventory. However, given the complexity of the relationships among the many factors or variables, such manual control generally results in significant inefficiencies, sub-optimal yields, production etc.

Thus, an operating challenge for biofuel production is to manage various sub-process, and possibly the entire system or process, to automatically respond to a constraint or disruption anywhere in the production system or process. As will be described herein, integrated model predictive control may be used to manage the biofuel production process in a substantially optimal manner, balancing various, and possibly competing, objectives of the sub-processes to approach, meet, and/or maintain an objective for the overall process, e.g., a global objective, also referred to as an optimization objective, and subject to one or more constraints, e.g., on the sub-processes, or with respect to the entire process. More specifically, model predictive control may be used to manage batch and continuous processes in an integrated manner to operate the biofuel production process in an optimal fashion, although it should be noted that traditionally batch and continuous operations must be managed independently because of the different temporal functions required to model these processes.

It should be noted that as used herein, the terms "maximum", "minimum", and "optimum", may refer respectively to "substantially maximum", "substantially minimum", and "substantially optimum", where "substantially" indicates a value that is within some acceptable tolerance of the theoretical extremum, optimum, or target value. For example, in one embodiment, "substantially" may indicate a value within 10% of the theoretical value. In another embodiment, "substantially" may indicate a value within 5% of the theoretical value. In a further embodiment, "substantially" may indicate a value within 2% of the theoretical value. In yet another embodiment, "substantially" may indicate a value within 1% of the theoretical value. In other words, in all actual cases (non-theoretical), there are physical limitations of the final and intermediate control element, dynamic limitations to the acceptable time frequency for stable control, or fundamental limitations based on currently understood chemical and physical relationships. Within these limitations the control system will generally attempt to achieve optimum operation, i.e., operate at a targeted value or constraint (max or min) as closely as possible.

Figure 7B:
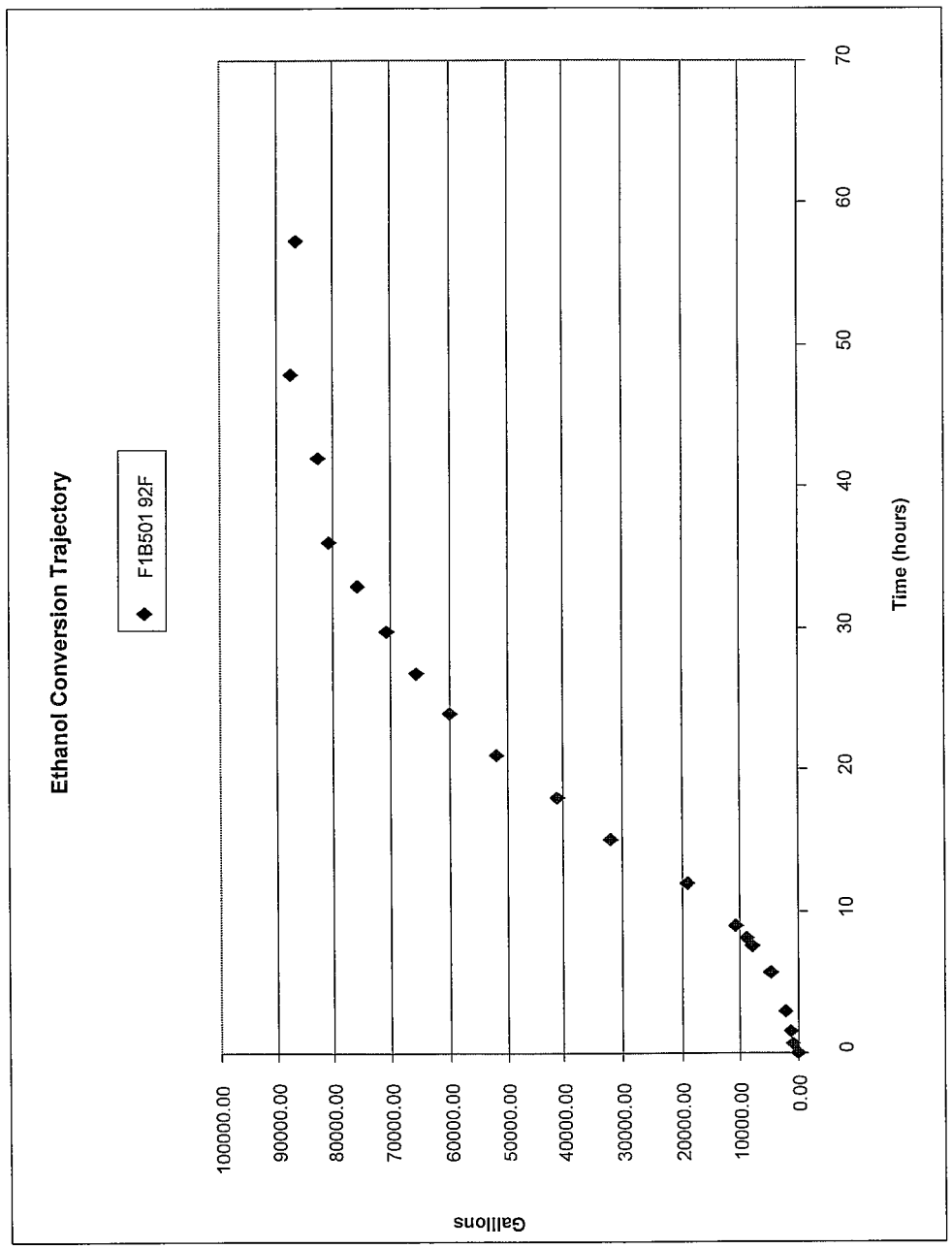
FIG. 7B illustrates an exemplary fermentation yield curve for a biofuel production process, according to one embodiment.

As noted above, the fermentation process in biofuel production is generally a batch process. As fermentation proceeds, more sugar in the fermentation mash or slurry is converted into biofuel. FIG. 7B illustrates an exemplary fermentation yield curve that illustrates such biofuel conversion over time. Note that the speed of conversion varies through the life of the batch; it starts slowly, increases, and then finally slows down towards the end of the batch. Note, however, that in general although not necessarily exclusively, the yield of bio-fuel product increases continuously through the process. As the fermentation time (i.e., batch time—the amount of time the fermentation materials are allowed to ferment in the fermentation vat) is increased, overall plant throughput rates generally have to be decreased because of inventory limitations in the system; however, longer fermentation times increase biofuel yield, and so there is a trade off to be made between throughput and biofuel yield.

This trade off between throughput and yield is non-linear in nature, time-variant, and dependent on fermentation characteristics. If the batch times are decreased, not only does the product rate to distillation process increase, since the fermentation product is available sooner and thus more often, but the fermentation feed rates must be increased to ensure batches are filled on time in keeping with the processing sequence. Conversely, if the batch times are increased, not only does the product rate to the distillation process decrease, but the fermentation feed rates must be slowed to match fermentation times. Thus, considerations that may be specific to a batch sub-process, such as fermentation, may entail changes with respect to continuous sub-processes, e.g., distillation/dehydration, cooking/milling, and/or stillage processing, and vice versa.

The following describes various embodiments of a system and method for integrated management of batch and continuous processes in a biofuel production process.

Exemplary MPC for Integrated Management of Batch and Continuous Processes in a Biofuel Production Process As noted above, model predictive control may be used to manage batch and continuous processes in an integrated manner to operate the biofuel production process in an optimal fashion, but in prior art approaches, batch and continuous operations have been managed independently because of the different temporal functions required to model these processes. However, embodiments of the present invention may facilitate optimization of such processes or sub-processes conjunctively by integrating the models via a framework or system that ameliorates the temporal incompatibilities between batch and continuous processes. This type of framework or system is referred to herein as a "continuous simulation framework", although this particular term is not intended to limit the invention to any particular form or function. Various embodiments of such a framework used to merge the batch behavior with the continuous behavior in a simultaneous optimization are now described.

The temporal incompatibilities between batch and continuous processes are due to the fact that batch production increases in a nonlinear temporal fashion as a function of batch time (time since batch start), but continuous process operations can be continuously be optimized against a variety of varying conditions that vary with equipment conditions, feedstock quality and ambient/energy system conditions. To bridge these different process relations the batch-time dependent parameters may be transformed into an equivalent continuous processing simulation system via one or more bridging equations or transforms, various embodiments of which are described herein. In preferred embodiments, the framework includes the bridging equations.

One approach is to create a virtual continuous plant model that simulates continuous batch feedstock and energy consumption and interfaces smoothly with continuous production from the batch plant equipment. In other words, the batch process may be simulated as a virtual continuous process. In this way, the demands on the continuous plant equipment may be calculated based on varying performance of the batch plant sections represented in this virtual continuous simulation.

In one exemplary embodiment, consider three batch fermenters that run in series. These fermenters may be sequentially filled, processed, and drained to a product tank. Each fermenter is filled in series so that at any one time one of the three fermenters is being filled, and so filling proceeds in a continuous manner (e.g., fermenter A, then B, then C, then A again, and so on). After filling, each batch fermenter processes biomass and produces biofuel.

Figure 8:
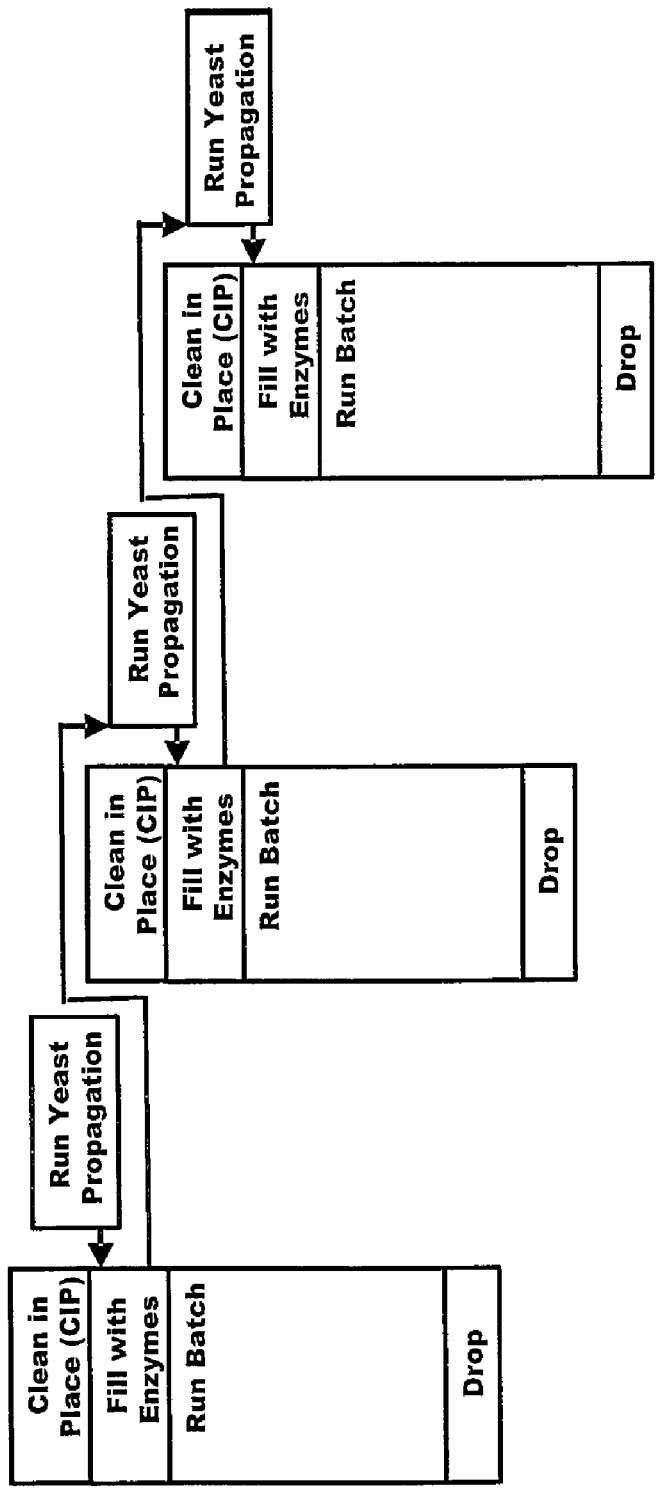
FIG. 8 illustrates exemplary fermentation batch cycles in a biofuel production process, according to one embodiment.

FIG. 8 illustrates an exemplary multi-fermenter system, where the fermenters are operated in this manner. As may be seen, each batch is operated somewhat separately, but may include some interaction with the other batches, e.g., providing enzymes for subsequent fermenters in the sequence. Note that in this case, the processing time for each fermenter (which includes fill time, because the fermentation proceeds during filling) is three times the filling time minus the time to drain a fermenter. Thus, for example, if the filling time is F and the draining time is D then each batch occurs over the time period of 3F−D. In this example while draining is not occurring continuously (it occurs for this shorter period D), each fermenter is drained into a common product tank that is continuously drained to feed a continuously operated downstream process (e.g. distillation). Thus, if at the end of each batch each fermenter makes the same volume of product, V, at the same target biofuel concentration, Y, then the equivalent virtual continuous production of biofuel may be determined thusly: 3 fermenters times their volume, V, times their concentration, Y, divided by the fermentation completion cycle (time), in this case, 3F, and so the (virtual) continuous biofuel production from the three batch fermenters is equal to 3V*Y/3F. Thus, this bridging equation or transform allows modeling of fermentation batch production as a virtual continuous production process.

Similarly, an equivalent continuous production of biomass, stillage, and water may be represented as 3V/3F or V/F. The equivalent consumption of feed relates to the feed volume, which may be higher than the completion volume (e.g. through evaporation and $CO_2$ exhaust) such that the continuous feed of biomass slurry is 3V'/3F, where V' is the initial filled fermentation volume. Using techniques described in U.S. provisional application Ser. No. 60/863,759 titled "Model Predictive Control of a Biofuel Production Process" and/or U.S. Provisional Application Ser. No. 60/917,916 titled "Nonlinear Model Predictive Control of a Biofuel Fermentation Process", both of which were incorporated by reference above, end of batch targets or optimization results along with fermentation volumes (fixed or calculated as part of the batch optimization) and the fermentation timing may be used as conversion parameters or transforms between continuous and batch calculations.

Thus, in this example, as one possible solution, a common framework for calculation and optimization may be achieved and classical optimization techniques may be utilized for integrated optimization across combined batch and continuous process operations. Similarly, where batch optimization uses optimized and controlled trajectories of enzyme volumes to support batch operations and optimized and controlled trajectories of temperature targets, and therefore cooling demand, these aspects may be calculated across each batch as a batch total and may be averaged (e.g. average enzyme consumption rate as a function of global batch/continuous process operations) or calculated at maximums and demand limits (e.g. maximum cooling demand and availability as a constraint of the global optimization), although it should be noted that these examples are meant to be exemplary only, and are not intended to limit the bridging equations or transforms to any particular form or function.

In another embodiment, this same concept of calculating a virtual continuous framework from batch process operations to enable simultaneous or integrated optimization across batch and continuous operations may be accomplished without reliance on virtual equivalent continuous plant simulations. In this alternative solution the batch calculation framework (nonlinear predictive model) used to optimize end of batch results (see U.S. provisional application Ser. No. 60/863,759 and/or U.S. Provisional Application Ser. No. 60/917,916) may be calculated within a simultaneous or integrated continuous optimization model. In this case, the same batch/continuous connections (e.g., material and energy bridges between continuous and batch process operations) may be connected in a simultaneous or integrated optimization system that optimizes both the batch and continuous plant sections in a common modeling framework simultaneously. The same modeling concepts may be leveraged as described above, although it should be noted that the solution is not accomplished by iterative passing of results and constraints between two parallel optimization solutions, but rather by iterative optimization on a simultaneous or integrated, common modeling framework, i.e., the integrated model described herein.

Figure 9:
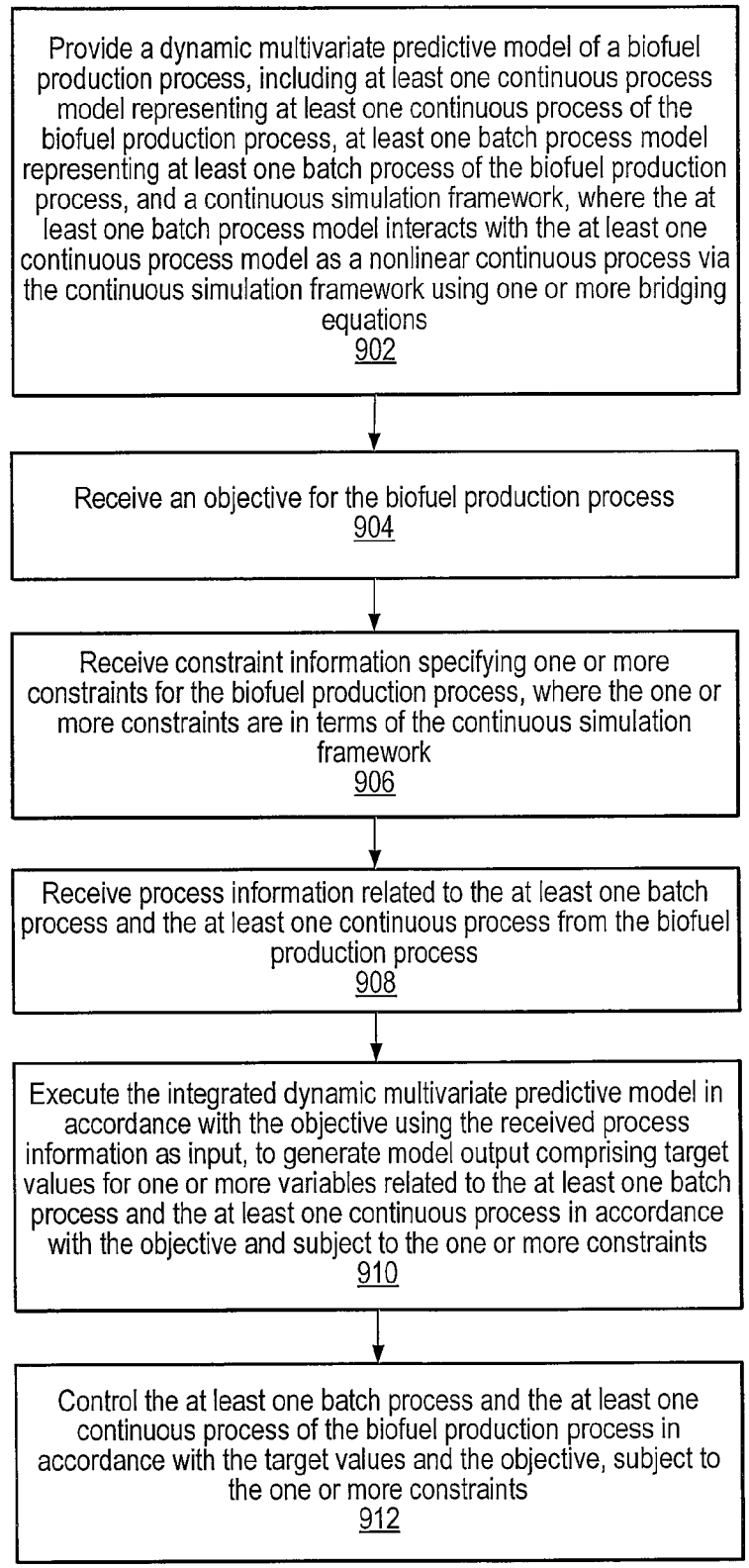
FIG. 9 is a high-level flowchart of a method for managing a plurality of sub-processes, including at least one continuous process and at least one batch process, of a biofuel production process utilizing model predictive control, according to one embodiment.

FIG. 9—Method for Integrated Model Predictive Control of a Biofuel Production Process FIG. 9 is a high-level flowchart of a method for integrated model predictive control of a biofuel production process, according to one embodiment. More specifically, embodiments of the method apply model predictive control techniques to manage multiple sub-processes of the biofuel production process in an integrated manner, particularly batch (e.g., batch fermentation) and continuous processes. Note that in various embodiments, various of the method elements may be performed concurrently, in a different order than shown, or may be omitted. Additional method elements may also be performed. As shown, this method may operate as follows.

In 902, an integrated dynamic multivariate predictive model representing a plurality of sub-processes of the biofuel production process may be provided. In a preferred embodiment, the integrated dynamic multivariate predictive model includes at least one continuous process model representing at least one continuous process of the biofuel production process, at least one batch process model representing at least one batch process of the biofuel production process, and a continuous simulation framework, where the at least one batch process model interacts with the at least one continuous process model as an equivalent virtual nonlinear continuous process via the continuous simulation framework using one or more bridging equations. In other words, as described above, the continuous simulation framework may facilitate integrated modeling of the at least one batch process and the at least one continuous process by allowing the at least one batch process model to interact or interface with the at least one continuous process model in such a way that the at least one batch process model represents the at least one batch process as a virtual continuous process. Said another way, the at least one batch process may be represented to the at least one continuous process model as a virtual continuous process, thus facilitating interactions between the at least one batch process model and the at least one continuous process model in continuous process terms.

Note that, as discussed above, in some embodiments, the at least one batch process model models the at least one batch process as the nonlinear continuous process using the one or more bridging equations. In other words, the at least one batch process model may use the bridging equations or transforms to model the at least one batch process as one or more continuous processes. Thus, in some embodiments, the framework may be part of the at least one batch process model.

In an alternative embodiment, the at least one batch process model may interact with the at least one continuous process model through the one or more bridging equations, where the one or more bridging equations include transforms that translate batch parameters to continuous parameters. This may allow the at least one batch process model and the at least one continuous process model to respond simultaneously to the process information, i.e., may allow the models to operate on a common ground. Thus, in some embodiments, the framework may operate as a translation interface for the at least one batch process model, allowing it to appear to or interact with the at least one continuous process as a continuous process model itself.

In other words, in both of these approaches, the framework allows both models to respond to process information in common terms, specifically, in continuous process terms, despite the batch nature of the at least one batch process.

In some embodiments, the at least one batch process may include or be a batch fermentation process for the biofuel production process, which, as described above, processes the fermentation mash or slurry in batches (in one or more fermentation vats or tanks). The at least one continuous process may include one or more continuous process of the biofuel production process, such as, but not limited to: a cooking and milling process (i.e., the fermentation feed, including upstream sources), a distillation and dehydration process, and/or a stillage process, among others.

In 904, an objective for the biofuel production process may be received, e.g., specifying or encoding a desired behavior or outcome of the biofuel production process. In some embodiments, the objective may be complex or compound. For example, the objective may include a global objective, and a plurality of sub-objectives directed to at least a subset of the plurality of sub-processes, including the at least one batch process and the at least one continuous process. Said another way, the objective may include an overall objective for the biofuel production process, e.g., maximize throughput, efficiency, etc., and may also include various subsidiary objectives related specifically to the respective sub-processes, or combinations of sub-processes. Note that these sub-objectives may in some cases be mutually exclusive or competitive with respect to one another and/or with respect to the global objective. Additional sub-objectives related to other, e.g., secondary, goals of the production process may also be included in the objective as desired.

Exemplary objectives may include, but are not limited to, one or more operator specified objectives, one or more predictive model specified objectives, one or more programmable objectives, one or more target feed rates, one or more cost objectives, one or more quality objectives, one or more equipment maintenance objectives, one or more equipment repair objectives, one or more equipment replacement objectives, one or more economic objectives, a target throughput for the biofuel production process, one or more objectives in response to emergency occurrences, one or more dynamic changes in materials inventory information, and/or one or more dynamic changes in one or more constraints on the biofuels production process, among others.

In 906, constraint information specifying one or more constraints for the biofuel production process i.e., limitations on one or more aspects or variables of the biofuel production process, may be received, where in preferred embodiments, the one or more constraints are in terms of the continuous simulation framework. For example, the constraints may be in terms of continuous process parameters or variables, including, for example, virtual continuous parameters use to model or represent, or communicate with, the batch process as a continuous process, as described above.

The one or more constraints may include any such limitation on the production process, including, for example, but not limited to, one or more of: batch constraints, e.g., fermentation time, water constraints, feed constraints, equipment constraints, capacity constraints, temperature constraints, pressure constraints, energy constraints, market constraints, economic constraints, environmental constraints, legal constraints, and/or operator imposed constraints, among others. Examples of equipment constraints may include, but are not limited to, one or more of: operating limits for pumps, operational status of pumps, tank capacities, operating limits for tank pressures, operational status of tanks, operating limits for valve pressures, operating limits for valve temperatures, operating limits for pipe pressures, operating limits for energy provision, and/or operating limits for molecular sieves, among others. Moreover, in some embodiments, the constraint information may include dynamic constraint information. In other words, some (or all) of the constraints may change dynamically over time, and so the method may automatically adjust operations taking into account these changing constraints.

In 908, process information related to the plurality of sub-processes, including process information for the at least one batch process, and the at least one continuous process, may be received from the biofuel production process. This process information may be any type of process information, including state or condition information measured by sensors, (e.g., temperatures, pressures, real-time measurements of the biofuel in the fermentation system), computed algorithmically, inferred from models (i.e., inferential models), and/or lab values, and/or entered by operators, among others. This process information may further include equipment settings, flow rates, material properties, such as densities, content profiles, purity levels, ambient conditions, such as time of day, temperature, pressure, humidity, etc., economic or market conditions, such as cost of materials or product, and so forth. In other words, the process information may include any information that affects or influences any part of the biofuel production process.

For example, the process information may include measured attributes of the batch fermentation process, e.g., from sensors in the plant, laboratory data, e.g., from laboratory analysis results based on plant measurements, or predicted values for unmeasured attributes of the batch fermentation process computed by one or more predictive models, e.g., from virtual online analyzers (VOAs), described below with respect to the fermentation process.

In 910, the integrated dynamic multivariate predictive model may be executed in accordance with the objective using the received process information as input, to generate model output comprising target values for one or more variables related to the at least one batch process and the at least one continuous process in accordance with the objective and subject to the one or more constraints. In other words, the model may execute to determine target values for manipulated variables for the at least one batch process and the at least one continuous process that may be used to control the sub-processes in such a way as to attempt to meet the objective.

In 912, the plurality of sub-processes of the biofuel production process, including the at least one batch process and the at least one continuous process of the biofuel production process, may be controlled in accordance with the target values and the objective, subject to the one or more constraints. In other words, a controller (or a plurality of controllers) may modulate or otherwise control various operational aspects of the sub-processes in accordance with the target values of the manipulated variables, attempting to meet the objective, subject to the constraints. In some embodiments, the target values may simply be used as set points by the controller, i.e., the controller may set respective inputs of the various sub-processes to the respective target values. For example, controlling the plurality of sub-processes of the biofuel production process in accordance with the target values and the objective may include operating one or more controllers to control one or more of: one or more material feed rates, one or more water flows, one or more molecular sieve regenerations, one or more heat sources, and so forth, including any controllable aspects of the sub-processes useable to pursue and possibly meet the objective (or objectives).

The above receiving the objective, receiving process information, executing the integrated dynamic multivariate predictive model, and controlling, may be performed a plurality of times in an iterative manner to operate the biofuel production process in a substantially optimal fashion. In other words, the method described herein may be performed substantially continuously, i.e., at some specified frequency or in response to a schedule or events, providing online control of the biofuel production process in substantially real time to optimize the biofuel production process (with respect to the objective). In some embodiments, the constraint information may also be received iteratively, particularly in the case of dynamic constraints.

In some embodiments, executing the dynamic multivariate predictive model includes an optimizer executing the dynamic multivariate predictive model in accordance with the objective using the received process information and the one or more constraints as input, thereby generating the model output in accordance with the objective and subject to the one or more constraints. For example, in one embodiment, the optimizer may execute the dynamic multivariate predictive model a plurality of times in an iterative manner.

In embodiments where multiple objectives are provided, possibly at odds with one another, an optimizer may be used to balance the various sub-objectives in attempting to meet the global objective. In other words, an optimizer may be used to determine what, where, and when to compromise with respect to various of the sub-objectives in attempting to achieve or at least approach the global objective. Thus, in some embodiments, executing the dynamic multivariate predictive model may include an optimizer executing the dynamic multivariate predictive model to generate the model output, including the target values of one or more variables related to the at least one batch process and the at least one continuous process, in accordance with the global objective, and at least partially in accordance with the plurality of sub-objectives.

As noted above, in some embodiments, the optimizer may execute the dynamic multivariate predictive model a plurality of times in an iterative manner. For example, the optimizer may repeatedly execute the model under various inputs and compare the resulting outputs to the objective (including the sub-objectives), thereby searching the solution space for input configurations that optimize the outcome, e.g., that allow the global objective to be met or at least approached, while minimizing the compromises made with respect to the various sub-objectives.

Figure 10:
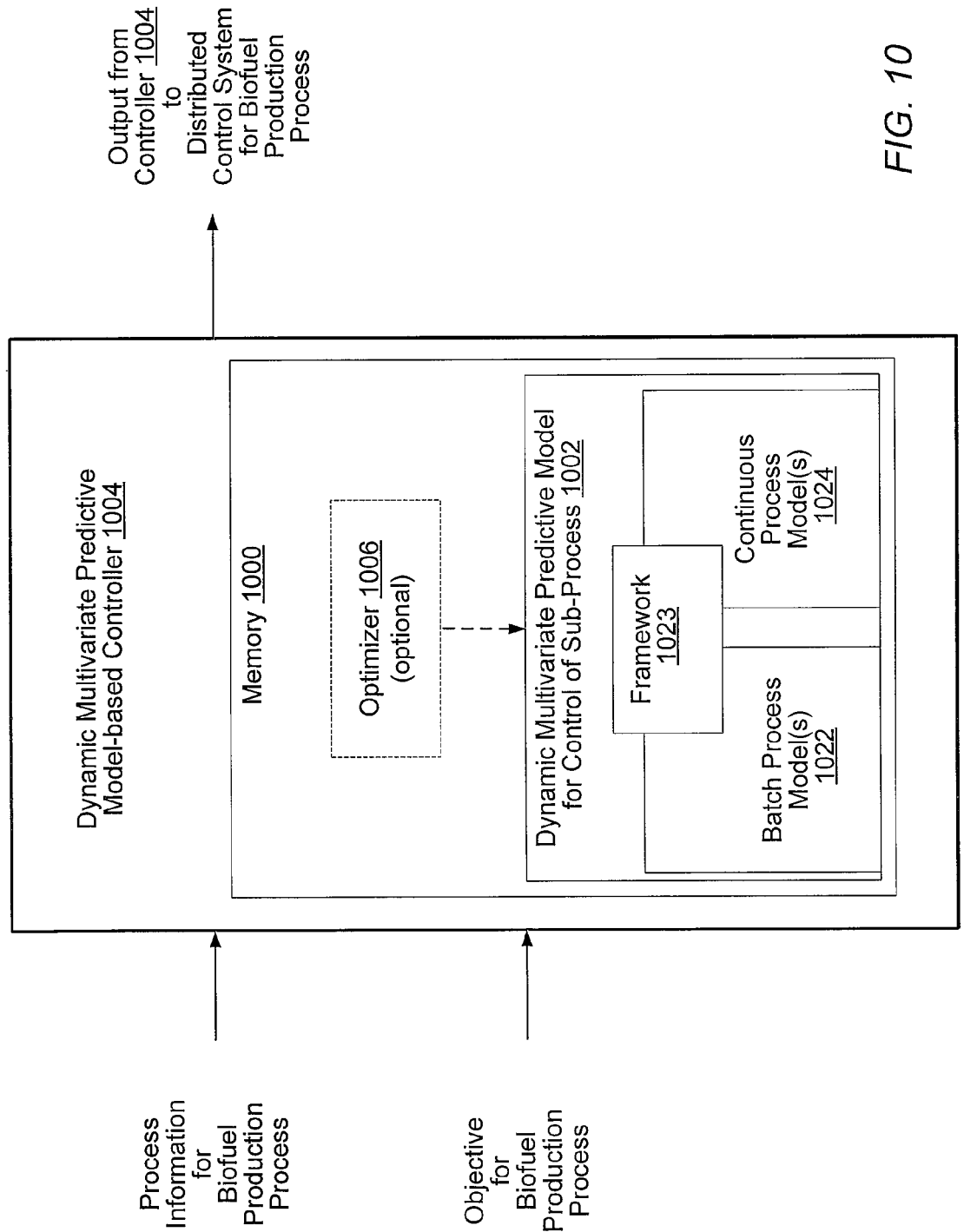
FIG. 10 illustrates exemplary integrated model predictive control of batch and continuous processes in a biofuel production process, according to one embodiment.

FIG. 10—Exemplary System for Integrated Model Predictive Control of a Biofuel Production Process FIG. 10 is a high-level block diagram of an exemplary system for performing embodiments of the method of FIG. 9. As FIG. 10 shows, the system may include a dynamic multivariate predictive model-based controller 1004, e.g., implemented using one or more computer systems. The controller 1004 may include a memory medium 1000 that stores an integrated dynamic multivariate predictive model that represents a plurality of sub-processes of the biofuel production process, including at least one batch process, and at least one continuous process. Note that the model may include various sub-models that represent the plurality of sub-processes involved in the biofuel production process or plant. For example, as FIG. 10 indicates, and as described above in method element 902 with reference to FIG. 9, the integrated dynamic multivariate predictive model may include at least one continuous process model 1022 representing at least one continuous process of the biofuel production process, at least one batch process model 1024 representing at least one batch process of the biofuel production process, and a continuous simulation framework 1023, where the at least one batch process model interacts with the at least one continuous process model as n equivalent virtual nonlinear continuous process via the continuous simulation framework using one or more bridging equations, examples of which are described above.

As shown, the controller 1004 may be operable to receive an objective, as well as process information for the biofuel production process, and produce output for controlling various operating parameters or variables of the biofuel production process or plant. In some embodiments, as mentioned above, the system may also include an optimizer 1006, coupled to the integrated dynamic model.

Embodiments of the above systems and methods may be operable to manage a plurality of sub-processes of the biofuel production process in an integrated manner to operate the biofuel process in a substantially optimal fashion.

Figure 11:
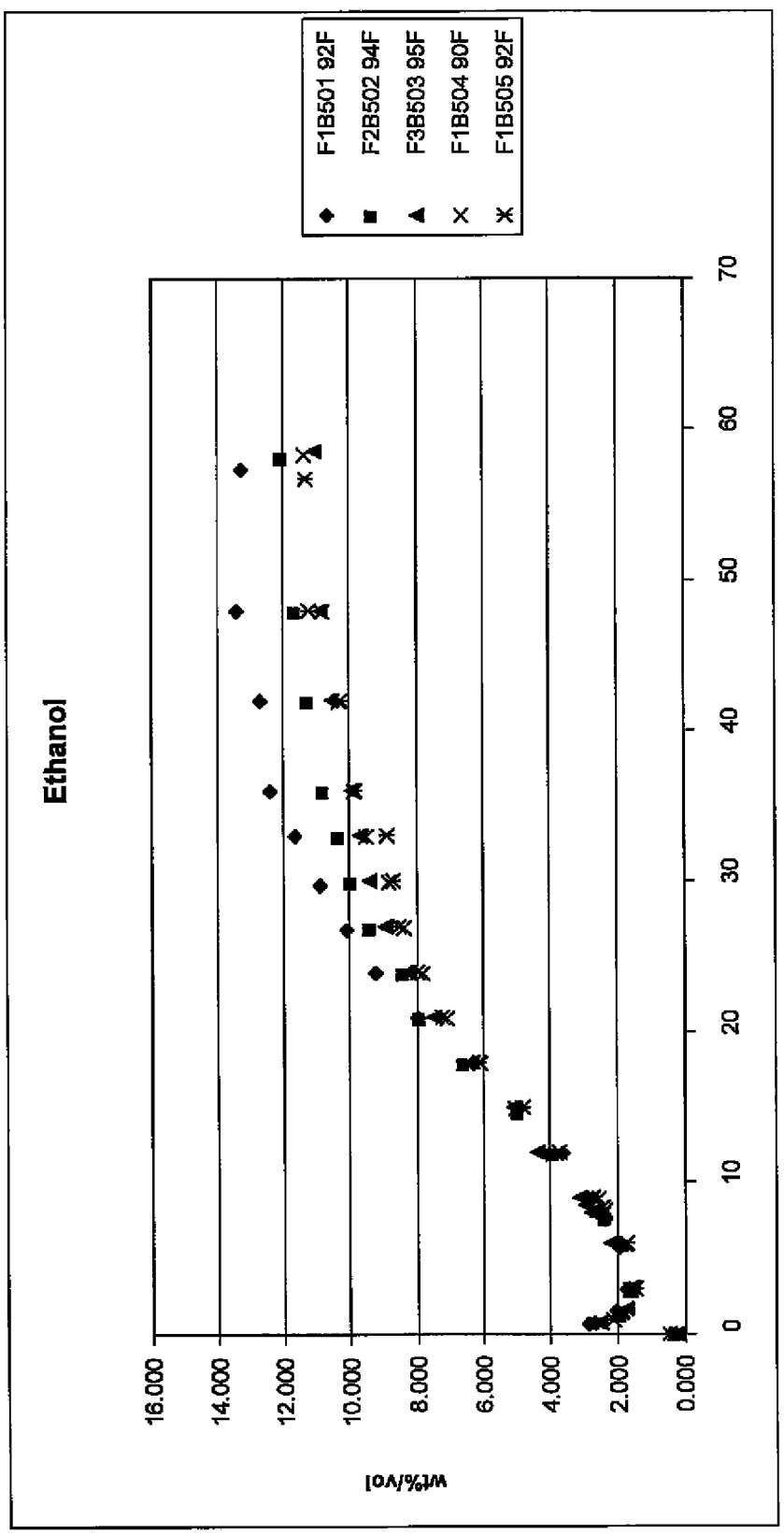
FIG. 11 illustrates exemplary trajectories of ethanol production from multiple batches with varying process conditions, according to one embodiment.

In some embodiments, the target values for manipulated variables may be in the form of trajectories, i.e., target trajectories. Thus, the biofuel process may be controlled in accordance with these trajectories to produce biofuel in a substantially optimum manner, resulting in corresponding ethanol production trajectories. FIG. 11 illustrates exemplary trajectories of ethanol production from multiple batches based on HPLC (High Purity Liquid Chromatography) laboratory testing, according to one embodiment. Note that the x-axis represents time in hours. As may be seen, the batches may differ substantially based on various parameters, e.g., temperature, among others. Thus, to optimize biofuel production across all the batches/fermenters, each fermenter may be controlled, where controlling each batch as a virtual nonlinear continuous process may provide for greater coordination of the batch processes with other, continuous, processes in the biofuel production process.

Figure 12:
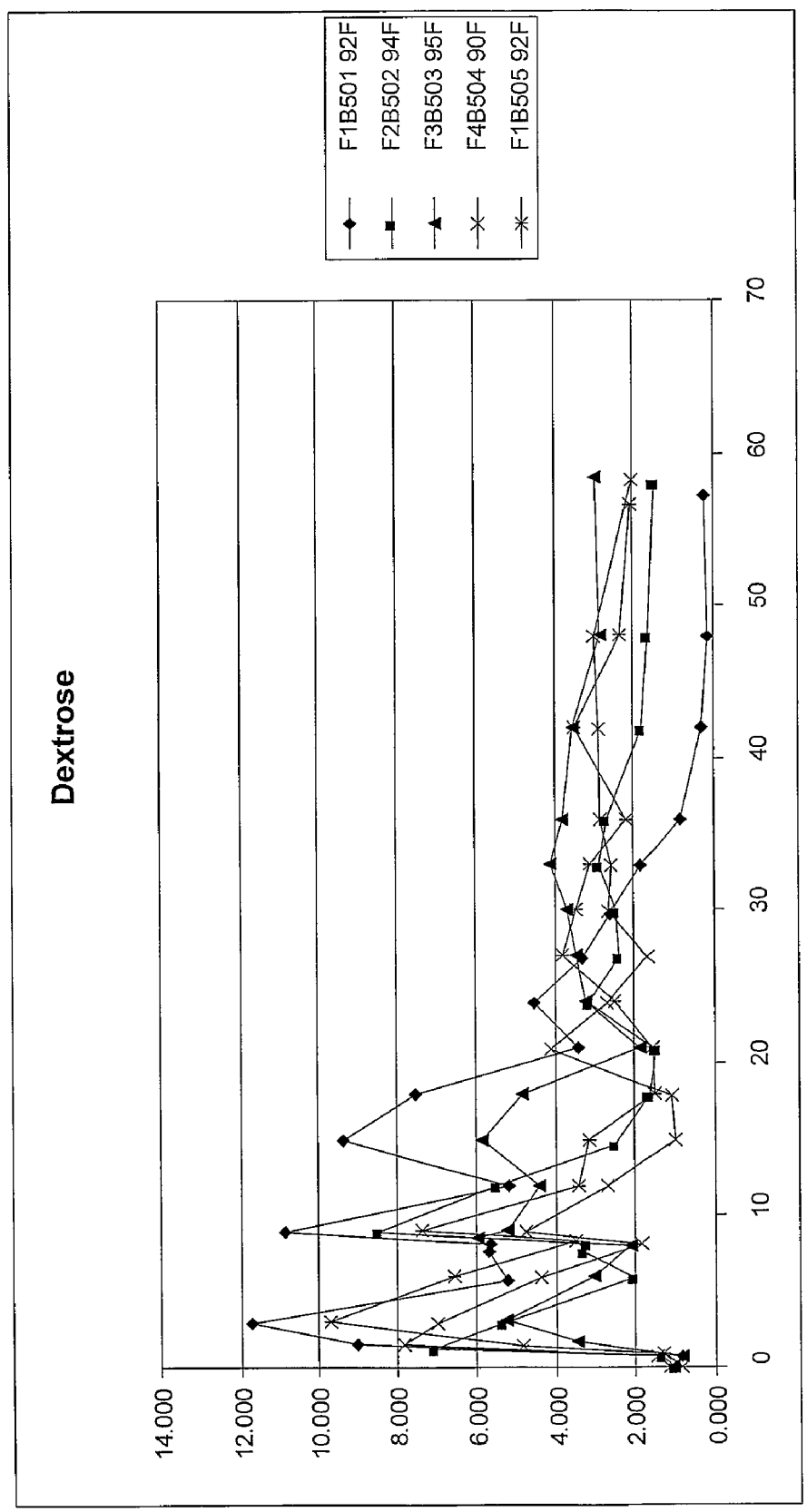
FIG. 12 illustrates exemplary trajectory of dextrose concentration from multiple batches, according to one embodiment.

FIG. 12 illustrates exemplary trajectories of dextrose concentration from multiple batches based on HPLC laboratory testing, according to one embodiment. Similar to the ethanol production trajectories of FIG. 11, the dextrose concentration trajectories differ substantially, e.g., based on production conditions, such as temperature, etc.

Figure 13:
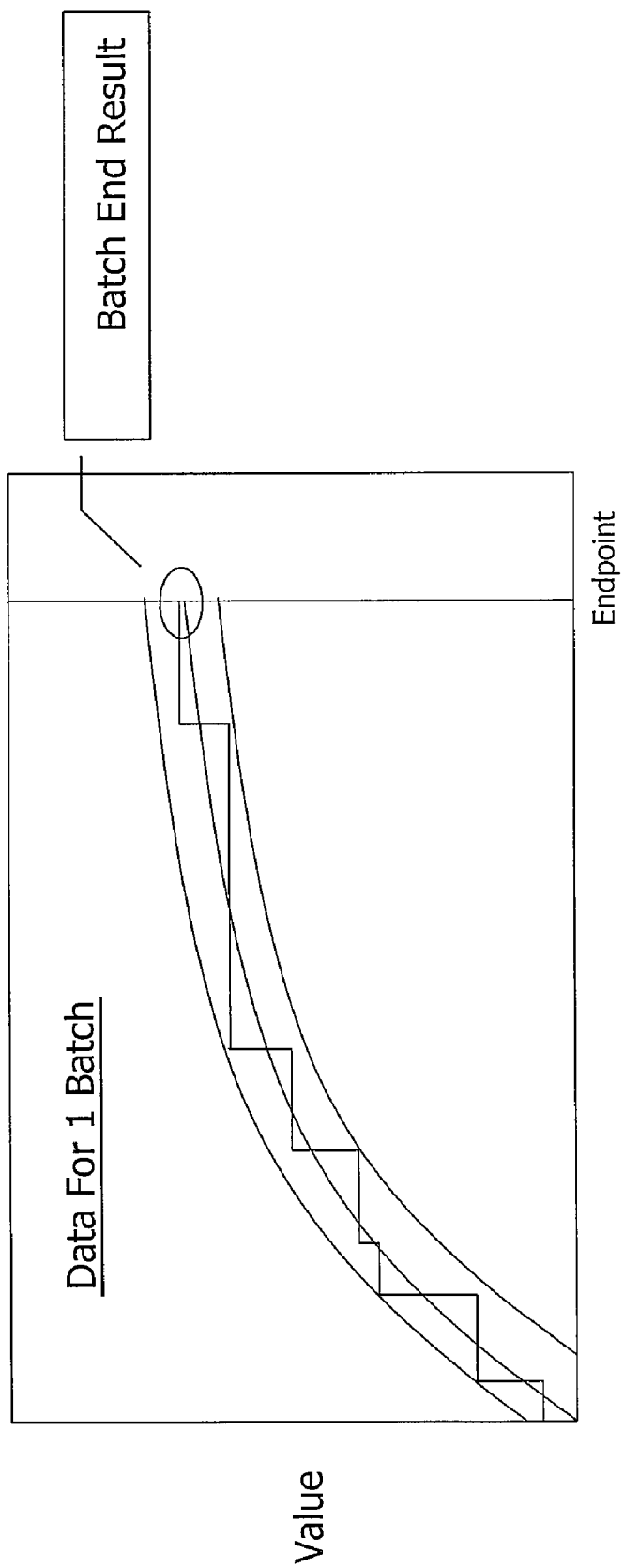
FIG. 13 illustrates an exemplary sample batch trajectory target for bio-fuel and intermittent manual concentration sampling, and controlling to that target trajectory, according to one embodiment.

FIG. 13 illustrates an exemplary sample batch trajectory target for bio-fuel and intermittent manual concentration sampling, according to one embodiment. In this figure, the middle curve is a target trajectory for ethanol concentration for the fermentation batch, and the stair-step curve represents the intermittent manual concentration sampling, i.e., these concentration values are obtained via sampling the fermentation process for the batch. As may be seen, based on the sampled values, the process is controlled to approach the target trajectory, in this case, staying between bounding "error" curves or tolerances.

It should be noted, however, that these FIGS. (11-13) are meant to be illustrative only, and are not intended to limit the application or results of the techniques described herein to any particular approach or outcome.

In some embodiments, the methods described herein may include managing some or all of the various described biofuel production sub-processes using model predictive control to produce biofuels in a substantially optimal fashion, i.e., in accordance with a specified global objective. For example, in one embodiment, the system, i.e., the optimizer, model, and/or controller, may receive and take into account some or all constraints of the fermentation batch process, the milling and cook processes, water-balance processes, distillation/sieve, and stillage units. The optimization objective (e.g., global objective) may integrate operating costs such as costs of production feedstocks, energy, catalysts, enzymes, and yield rate/trade-off. For the batch process, the system may have knowledge of the batch life of each vat (i.e., fermentation endpoint control). The system may then calculate a desired trajectory path (e.g., an ethanol trajectory path), which in turn may calculate desired targets for fermentation feed and condition adjustments. This trajectory may be set by an optimizer taking into account the dynamic constraints of all upstream and downstream units through the horizon of control of the process. The optimizer may also calculate the optimum trajectory of control action to keep the continuous process controlled within operating constraints and targets. For example, it may take into account that the fermentation product is sent to a surge inventory (e.g., a beer well) to feed distillation continuously. The system may then use model predictive control and optimization technology to measure or determine the system capacitance in the production system and project the optimum feed rates and fermentation cycle times.

Virtual Analyzers for the Biofuel Production Process

As indicated above, in some cases, there may be some attributes or variables of the biofuel production process that are not readily measurable. For example, to date, there are no reliable methods for online analysis of key fermentation variables, particularly ethanol concentration and dextrose concentration. In order to overcome this limitation, inferred property models, referred to as virtual analyzers (VOAs), have been developed to predict control variables needed by the above-described control strategy. More specifically, VOAs have been developed from process data and fundamental process knowledge to accurately predict key fermentation variables: ethanol concentration, dextrose concentration and yeast growth, although other VOAs may certainly be used as desired. Thus, in some embodiments, predicted values for unmeasured attributes of the batch fermentation process may be computed by one or more predictive models (e.g., VOAs). In some embodiments, these predictive models may be dynamic predictive models, e.g., where the models are dynamically updated, e.g., based on current process conditions. It should be noted that such VOAs may also be used with respect to any other processes or sub-processes of the biofuel production process as desired.

Thus, in some embodiments, the system may derive its measurements or process information from the process instruments or sensors, inferential models, real-time measurements of the biofuel in the fermentation system, and/or lab values, and execute linear or nonlinear dynamic prediction models to solve an overall "optimization objective"—typically an economic objective function subject to dynamic constraints of both the continuous and batch sections of the plant processes. The system may then execute the integrated (e.g., batch and continuous) dynamic multivariate predictive model/controller and optimizer in accordance with the objective, e.g., the optimization function. In one embodiment, the objective preferably includes two or more of the following: a biofuels production objective, the value of key inputs, biomass feedstock costs, the cost of enzymes, value of biofuels and stillage product(s), the quality specifications of measured end products, and measured constraints, among others. The system may then generate (model) outputs comprising of two or more of the following: fermentation feed rates, distillation feed rates, distillation feed inventory, and fermentation cycle times, all subject to specified constraints. Thus, the system may optimize one or more of: biofuel production rates, plant profit/cost function, yield of biofuels, enzyme per unit of biofuel, catalyst per unit of biofuel, energy per unit of biofuel, and/or the quality specifications of all end products, among others, and may do so subject to and respecting all specified constraints.

Thus, embodiments of the systems and methods described above may utilize model predictive control, and possibly optimization, to manage continuous and batch processes in a biofuel production process in an integrated manner to operate the biofuel process in a substantially optimal fashion.

Although the system and method of the present invention has been described in connection with the preferred embodiment, it is not intended to be limited to the specific form set forth herein, but on the contrary, it is intended to cover such alternatives, modifications, and equivalents, as can be reasonably included within the spirit and scope of the invention as defined by the appended claims.

We claim:

1. A computer-implemented method for managing a biofuel production process, comprising:
    providing an integrated dynamic multivariate predictive model that comprises:
        at least one continuous process model representing at least one continuous process of the biofuel production process;
        at least one batch process model representing at least one batch process of the biofuel production process; and
        a continuous simulation framework, wherein the at least one batch process model interacts with the at least one continuous process model as a nonlinear continuous process via the continuous simulation framework using one or more bridging equations;
    receiving an objective for the biofuel production process, wherein the objective comprises a global objective and a plurality of sub-objectives directed to the at least one batch process and the at least one continuous process;
    receiving constraint information specifying one or more constraints for the biofuel production process, wherein the one or more constraints are in terms of the continuous simulation framework;
    receiving process information related to the at least one batch process and the at least one continuous process from the biofuel production process;
    executing the integrated dynamic multivariate predictive model via an optimizer in accordance with the objective using the received process information as input, to generate model output comprising target values for one or more variables related to the at least one batch process and the at least one continuous process in accordance with the global objective and at least partially in accordance with the plurality of sub-objectives and subject to the one or more constraints; and
    controlling the at least one batch process and the at least one continuous process of the biofuel production process in accordance with the target values and the objective, subject to the one or more constraints.

2. The method of claim 1, wherein the at least one batch process model models the at least one batch process as an equivalent virtual nonlinear continuous process using the one or more bridging equations.

3. The method of claim 1, wherein the at least one batch process model interacts with the at least one continuous process model through the one or more bridging equations, wherein the one or more bridging equations comprise transforms that translate batch parameters to continuous parameters, allowing the at least one batch process model and the at least one continuous process model to respond simultaneously to the process information.

4. The method of claim 1, wherein said executing the dynamic multivariate predictive model comprises executing the dynamic multivariate predictive model via the optimizer in accordance with the objective using the received process information and the one or more constraints as input, thereby generating the model output in accordance with the objective and subject to the one or more constraints.

5. The method of claim 4, wherein executing the dynamic multivariate predictive model via the optimizer comprises executing the dynamic multivariate predictive model via the optimizer a plurality of times in an iterative manner.

6. The method of claim 1, wherein the constraint information comprises dynamic constraint information.

7. The method of claim 1, further comprising:
    performing said receiving the objective, said receiving process information, said executing the integrated dynamic multivariate predictive model, and said controlling, a plurality of times in an iterative manner to operate the biofuel production process in a substantially optimal fashion.

8. The method of claim 1, wherein the at least one batch process comprises a batch fermentation process for the biofuel production process.

9. The method of claim 1, wherein the at least one continuous process comprises one or more of:
    a cooking and milling process for the biofuel production process;
    a distillation and dehydration process for the biofuel production process; or
    a stillage process for the biofuel production process.

10. The method of claim 1, wherein the process information comprises one or more of:
    measured attributes of the batch fermentation process;
    laboratory data; or
    predicted values for unmeasured attributes of the batch fermentation process computed by one or more predictive models.

11. The method of claim 1, wherein said controlling the at least one batch process and the at least one continuous process of the biofuel production process in accordance with the target values and the objective comprises operating one or more controllers to control one or more of:
    one or more material feed rates;
    one or more water flows;
    one or more molecular sieve regenerations; or
    one or more heat sources.

12. A computer-accessible memory medium configured for managing a biofuel production process, wherein the memory medium stores:
    an integrated dynamic multivariate predictive model that comprises:
        at least one continuous process model representing at least one continuous process of the biofuel production process;
        at least one batch process model representing at least one batch process of the biofuel production process; and
        a continuous simulation framework, wherein the at least one batch process model interacts with the at least one continuous process model as a nonlinear continuous process via the continuous simulation framework using one or more bridging equations; and
    program instructions, executable by the processor to perform:
        receiving an objective for the biofuel production process, wherein the objective comprises a global objective and a plurality of sub-objectives directed to the at least one batch process and the at least one continuous process;

receiving constraint information specifying one or more constraints for the biofuel production process, wherein the one or more constraints are in terms of the continuous simulation framework;

receiving process information related to the at least one batch process and the at least one continuous process from the biofuel production process;

executing the integrated dynamic multivariate predictive model via an optimizer in accordance with the objective using the received process information as input, to generate model output comprising target values for one or more variables related to the at least one batch process and the at least one continuous process in accordance with the global objective and at least partially in accordance with the plurality of sub-objectives and subject to the one or more constraints; and controlling the at least one batch process and the at least one continuous process of the biofuel production process in accordance with the target values and the objective, subject to the one or more constraints.

13. The memory medium of claim 12, wherein the at least one batch process model models the at least one batch process as an equivalent virtual nonlinear continuous process using the one or more bridging equations.

14. The memory medium of claim 12, wherein the at least one batch process model interacts with the at least one continuous process model through the one or more bridging equations, wherein the one or more bridging equations comprise transforms that translate batch parameters to continuous parameters allowing the at least one batch process model and the at least one continuous process model to respond simultaneously to the process information.

15. The memory medium of claim 12, wherein said executing the dynamic multivariate predictive model comprises executing the dynamic multivariate predictive model via the optimizer in accordance with the objective using the received process information and the one or more constraints as input, thereby generating the model output in accordance with the objective and subject to the one or more constraints.

16. The memory medium of claim 15, wherein executing the dynamic multivariate predictive model via the optimizer comprises executing the dynamic multivariate predictive model via the optimizer a plurality of times in an iterative manner.

17. The memory medium of claim 12, wherein the program instructions are further executable to perform:
    performing said receiving the objective, said receiving process information, said executing the integrated dynamic multivariate predictive model, and said controlling, a plurality of times in an iterative manner to operate the biofuel production process in a substantially optimal fashion.

18. The memory medium of claim 12,
    wherein the at least one batch process comprises a batch fermentation process for the biofuel production process, and
    wherein the at least one continuous process comprises one or more of:
        a cooking and milling process for the biofuel production process;
        a distillation and dehydration process for the biofuel production process; or
        a stillage process for the biofuel production process.

19. The memory medium of claim 12, wherein the process information comprises one or more of:
    measured attributes of the batch fermentation process;
    laboratory data; or
    predicted values for unmeasured attributes of the batch fermentation process computed by one or more predictive models.

20. The memory medium of claim 12, wherein said controlling the at least one batch process and the at least one continuous process of the biofuel production process in accordance with the target values and the objective comprises operating one or more controllers to control one or more of:
    one or more material feed rates;
    one or more water flows;
    one or more molecular sieve regenerations; or
    one or more heat sources.

21. A system for managing sub-processes in a biofuel production process, comprising:
    a processor; and
    a memory medium coupled to the processor, wherein the memory medium stores:
        an integrated dynamic multivariate predictive model that comprises:
            at least one continuous process model representing at least one continuous process of the biofuel production process;
            at least one batch process model representing at least one batch process of the biofuel production process; and
            a continuous simulation framework, wherein the at least one batch process model interacts with the at least one continuous process model as a nonlinear continuous process via the continuous simulation framework using one or more bridging equations; and
        program instructions, executable by the processor to:
            receive an objective for the biofuel production process, wherein the objective comprises a global objective and a plurality of sub-objectives directed to the at least one batch process and the at least one continuous process;
            receive constraint information specifying one or more constraints for the biofuel production process, wherein the one or more constraints are in terms of the continuous simulation framework;
            receive process information related to the at least one batch process and the at least one continuous process from the biofuel production process;
            execute the integrated dynamic multivariate predictive model via an optimizer in accordance with the objective using the received process information as input, to generate model output comprising target values for one or more variables related to the at least one batch process and the at least one continuous process in accordance with the global objective and at least partially in accordance with the plurality of sub-objectives and subject to the one or more constraints; and
            control the at least one batch process and the at least one continuous process of the biofuel production process in accordance with the target values and the objective, subject to the one or more constraints.

22. The system of claim 21, wherein the at least one batch process model models the at least one batch process as an equivalent nonlinear continuous process using the one or more bridging equations.

23. The system of claim 21, wherein the at least one batch process model interacts with the at least one continuous process model through the one or more bridging equations, wherein the one or more bridging equations comprise transforms that translate batch parameters to continuous parameters, allowing the at least one batch process model and the at least one continuous process model to respond simultaneously to the process information.

* * * * *